(12) United States Patent
Alchenberger et al.

(10) Patent No.: US 11,639,484 B2
(45) Date of Patent: May 2, 2023

(54) PERFUME COMPOSITIONS

(71) Applicant: GIVAUDAN SA, Vernier (CH)

(72) Inventors: Alain Alchenberger, Zürich (CH); Christian Quellet, Biel (CH)

(73) Assignee: GIVAUDAN SA, Vernier (CH)

( * ) Notice: Subject to any disclaimer, the term of this patent is extended or adjusted under 35 U.S.C. 154(b) by 320 days.

(21) Appl. No.: 16/527,980

(22) Filed: Jul. 31, 2019

(65) Prior Publication Data

US 2019/0382684 A1    Dec. 19, 2019

Related U.S. Application Data

(62) Division of application No. 15/311,366, filed as application No. PCT/EP2015/061756 on May 27, 2015, now abandoned.

(30) Foreign Application Priority Data

May 27, 2014    (GB) ..................... 1409348

(51) Int. Cl.
*G01N 33/00* (2006.01)
*C11B 9/00* (2006.01)
*B05B 11/06* (2006.01)

(52) U.S. Cl.
CPC ............ *C11B 9/0092* (2013.01); *B05B 11/06* (2013.01); *C11B 9/00* (2013.01); *C11B 9/0015* (2013.01); *C11B 9/0019* (2013.01); *C11B 9/0023* (2013.01); *C11B 9/0034* (2013.01); *C11B 9/0076* (2013.01); *G01N 33/0016* (2013.01); *G01N 33/0021* (2013.01); *G01N 33/0001* (2013.01)

(58) Field of Classification Search
None
See application file for complete search history.

(56) References Cited

U.S. PATENT DOCUMENTS

| 2,976,327 | A | 3/1961 | Julian et al. |
| 3,981,892 | A | 9/1976 | Skorianetz |
| 4,313,856 | A | 2/1982 | Kaiser et al. |
| 4,709,061 | A | 11/1987 | Ernst-Joachim et al. |
| 5,948,812 | A | 9/1999 | Kraft |
| 6,184,419 | B1 | 2/2001 | Berg-Schultz et al. |
| 6,467,332 | B1 * | 10/2002 | Bertschi ............ G01N 33/0031 73/865.6 |
| 2001/0031710 | A1 | 10/2001 | Margot |

(Continued)

FOREIGN PATENT DOCUMENTS

| EP | 0294746 A1 | 12/1988 |
| EP | 1098195 A2 | 5/2001 |

(Continued)

OTHER PUBLICATIONS

EP Search Report for corresponding application EP 19165214.8 dated May 24, 2019.

(Continued)

*Primary Examiner* — Arrie L Reuther
(74) *Attorney, Agent, or Firm* — Norris McLaughlin PA

(57) ABSTRACT

Perfume compositions having controlled spatio-temporal olfactory profiles are described. The disclosure also relates also to a method of measuring said spatial-temporal olfactory profiles of said compositions.

12 Claims, 2 Drawing Sheets

(56) References Cited

U.S. PATENT DOCUMENTS

| | | | |
|---|---|---|---|
| 2008/0234172 A1 | 9/2008 | McGee et al. | |
| 2009/0130934 A1 | 5/2009 | Schmidt et al. | |
| 2009/0320559 A1* | 12/2009 | Lemieuvre | G01N 1/22 73/863.11 |
| 2012/0247182 A1 | 10/2012 | Nelson | |

FOREIGN PATENT DOCUMENTS

| | | |
|---|---|---|
| JP | 2001002618 A | 1/2001 |
| JP | 2001316316 A | 11/2001 |
| JP | 2010126729 A | 6/2010 |
| WO | 2007045862 A1 | 4/2007 |
| WO | 2014029695 A1 | 2/2014 |

OTHER PUBLICATIONS

International Search Report for corresponding application PCT/EP2015/061756 dated Nov. 6, 2015.

GB Search Report for corresponding application GB1409348.8 dated Nov. 28, 2014.

\* cited by examiner

PERFUME COMPOSITIONS

This is a Divisional patent application of U.S. Ser. No. 15/311,366 filed, 15 Nov. 2016, which in turn is an application filed under 35 USC 371 of PCT/EP2015/061756 filed on 27 May 2015, which in turn claims priority to GB 1409348.8 filed 27 May 2014. The applicant claims all available priority benefits to the foregoing, and incorporates by reference the entirely of the foregoing as if set forth herein.

This disclosure relates to perfume compositions having controlled spatio-temporal olfactory profiles. More particularly, this disclosure relates to perfume compositions having coherent, fast developing and prolonged olfactory impact at a distance from the compositions' source, when submitted to convection flows. The disclosure also relates to a method of measuring said spatial-temporal olfactory profiles of said compositions.

Fragrance in an atmosphere or sprayed on to a substrate (including skin) is often desired for a number of aesthetic and practical reasons, for example, to freshen air, to provide an attractive personal fragrance, or a particular mood or ambience in a room. Over the centuries, perfumers have developed the art of achieving the proper aesthetic effect by mixing a broad range of ingredients having various olfactive characteristics, volatilities and intensities, in a similar way as painters mix their colours to realize masterworks. This art has remained essentially empirical.

More recently, attempts have been made to develop perfumery rules based on ingredient physicochemical properties, such as boiling point, vapour pressure, or polarity, and sensory properties, such as odour detection threshold.

The relationship between vapour pressure and odour detection threshold (ODT) has been known for several decades. The so-called "Odour Value", which is simply the ratio of headspace concentration of an odourant to the odour detection threshold is a convenient way to combine these two latter properties into a unique and quantitative measure of odour strength, which enables one to discriminate between odorants that are substantive, i.e. which can be perceived on a substrate for a long period of time and those which are elusive, i.e. which vanish rapidly, as well as between odorants which are impactful and those which are weak.

With regard to a fragrance composition that is diluted in water, under such conditions the instantaneous impact of an odourant is proportional to that odourant's volatility (or its so-called "acceleration" in water) and inversely proportional to its threshold.

However, both of these observations are concerned with a perfume's properties close to its source and not with how the perfume performs at a relatively large distance from the source.

The impact of a perfume at a distance from its source is often referred to as the "volume", or if directional convection flows are present, as "trail" or "sillage" of that perfume. Sillage has always been considered to be of interest, particularly in the fields of personal or fine fragrances. The ability of a perfume to be recognised in a space some distance from its source is an important characteristic of a perfume. It is surprising that there are no adequate methods of evaluating the trail aspects of perfumes, and perfumers are generally content to evaluate their creations by applying them to blotters and smelling them at close range, typically at a distance of 5 to 10 centimetres; or by evaluating the ability of an odour to fill a space defined in a smelling booth, which provides an assessment of the quantity of odour which has accumulated in a booth between the moment when the odour source was delivered to the booth and the moment of its detection or observation. Such an assessment is essentially static.

The skilled person will appreciate that convection is the major driver of the transport of odorants through the air. The skilled person will also understand that all odorants will be transported coherently through the air by convection flows, i.e. with roughly the same velocity, and that the average velocity of each odorant at any point of the space is the same as that of the convection flow itself at this point of space.

The skilled person will also understand that the perceived intensity of that odourant at distance will be proportional to its partial Odour Value, i.e. the Odour Value of the pure odourant multiplied by its effective concentration at that distance.

It follows from this that the skilled person will appreciate that by selecting odourants in a certain operative window of volatility and odour detection threshold (ODT), it must be possible to predict an olfactory effect at some distance from a perfume source.

Whereas the skilled person would understand that coherent movement of perfume ingredients in a convection flow and detection are based on Odour Detection Threshold and vapour pressure considerations, the applicant has found that a simple consideration of these factors is not predictive of perfume composition performance under conditions of trail.

There remains a need to provide methods of odour evaluation, which answer to true life conditions of trail in order to differentiate perfumes based on their trail characteristics, and to develop rules of perfume selection that enables one to select perfume ingredients on the basis of their being trail drivers, and to create new perfumes optimised for trail. There is also a need for new perfume compositions that exhibit coherent, fast developing and prolonged olfactory impact, at some distance from a perfumed object.

Applicant has found that perfume ingredients may be grouped in time-dependent relationship to form perfume compositions in such a way that when placed in a directional convection flow, the nature and olfactory profile of that perfume composition can be detected at a distance from its source with a reliable and recognisable odour.

Figure 1:
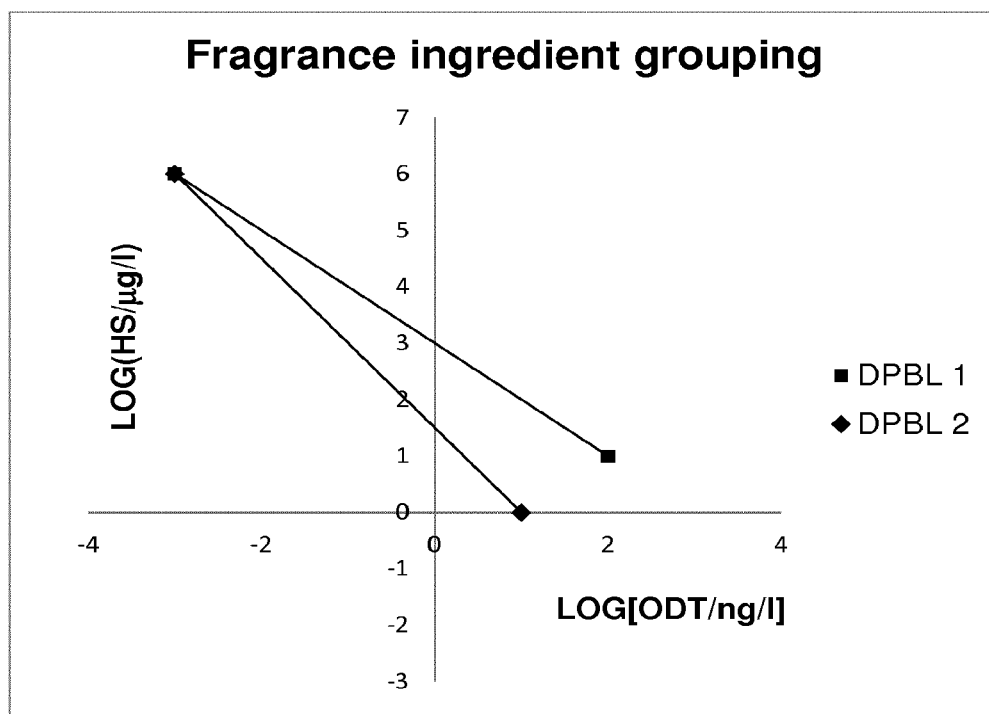
FIG. 1 is a graph illustrating a critical line in a standard equilibrium headspace concentration vs. odour detection threshold plot, whose coordinates are obtained by equations (1), disclosed hereinafter.

In a first aspect of the present invention there is provided a method of determining the spatial-temporal olfactory profile of fragrances.

In another aspect of the present invention there is provided a method of creating a perfume composition such that when placed in a directional convection flow, the nature and olfactory profile of that perfume composition can be detected at a distance from its source with a reliable and recognisable odour.

In still another aspect of the present invention there is provided a perfume composition that 30 when placed in a directional convection flow, the nature and olfactory profile of that perfume composition can be detected at a distance from its source with a reliable and recognisable odour.

In yet another aspect of the present invention there is provided a fine perfume, personal care composition or home care composition comprising a perfume composition defined herein.

Details of one or more embodiments of this invention are set forth in the following description. Other features, objects and advantages of the invention will be apparent from the following description and claims.

The invention is based on the surprising discovery that time also plays a key role in the perception of perfume ingredients at distance. In particular, it has now been found that the perception of ingredients at distance is characterized by two consecutive characteristic perception times, which are referred to in the following as "detection time" Td and "recognition time" Tr (i.e. the time where the smell has reached its maximum and does not change anymore, at least within the time frame of the evaluation experiment as it is defined hereunder).

More particularly, applicant has found that some ingredients are characterized by an extremely short detection time and are recognizable almost immediately, while other ingredients take more time to be detected and even more to be recognized. Finally, applicant has found that some perfumes and perfumery ingredients remain perceivable in the scented plume emanating from a source for a long time, even at some distance from the source, while others disappear shortly after having been perceived at the same distance. Contrary to the understanding of the skilled person, this time-dependent behaviour cannot be explained from merely volatility and odour detection threshold considerations.

Although a consideration of vapour pressure and odour detection threshold does not itself explain the concept of trail, the applicant has found that in order to be perceived at distance, a perfumery ingredient must have certain combinations of vapour pressure and odour detection threshold.

In particular, applicant has found that, in order to be perceived at distance, the standard equilibrium headspace concentration ($HS_i^0$) expressed in microgram/l, and the odour detection threshold ($ODT_i$), expressed in nanogram/l, of a pure ingredient must lie on or below a critical line in a standard equilibrium headspace concentration vs. odour detection threshold plot (see FIG. 1), wherein the coordinates of this critical line on this plot are obtained by equations (1)

$$A=[\log(ODT_a);\log(HS_a)] \text{ and } B=[\log(ODT_b); \log(HS_b)]$$

The plot referred to above and shown in FIG. 1 defines a straight line, having a negative slope in a log $HS_i^0$ vs. log $ODT_i$ plot, which is referred to hereinafter as the "distance perception boundary line" (DPBL) or "isoradiance line". The term "log" in equation (1) and throughout the disclosure refers to the decimal logarithm.

The term "standard equilibrium headspace concentration" used herein above refers to the concentration of the ingredient in equilibrium with the condensed form, that is, solid or liquid form of this ingredient at a temperature of 25° C. and under a pressure of 1 atmosphere. It can be measured by using any of the known quantitative headspace analysis techniques, see for example Mueller and Lamparsky in Perfumes: Art, Science and Technology, Chapter 6 "The Measurement of Odors" at pages 176-179 (Elsevier 1991).

The term Odour Detection Threshold ($ODT_i$) used herein above refers to the average concentration above which an odourant i can be perceived by a panelist and can be measured by olfactometry, as described, for example in Mueller and Lamparsky (op. cit).

Typically, the equilibrium headspace concentration may be measured as follows: 500 mg of the test compound is added to a headspace container which is then sealed. The container is then incubated at constant 25° C. until the compound reached equilibrium between the gas and the liquid phase. A defined volume of this saturated headspace (usually 0.5-1 lt) is trapped on a micro filter using Porapak Q as sorbent. After filter extraction with an appropriate solvent (usually 30-100 microliters methyl tert. butyl ether), an aliquot of the extract is analyzed by GC. Quantification is performed by the external standard calibration method. The concentration in the original headspace can be calculated (in terms of microgram/l) from the headspace volume sucked through the micro filter and the aliquot of the filter extract injected into the gas chromatograph. The final headspace concentration value of a given test compound is obtained as the mean value of three independent measurements each. Further information of the technique hereinabove described may be found in the article of Etzweiler, F.; Senn E. and Neuner-Jehle N., *Ber. Bunsen-Ges. Phys. Chem.* 1984, 88, 578-583.

The Odour Detection Threshold ($ODT_i$) may be measured by using an olfactometer.

The olfactometer functions on the principle of a linear dilution of an odorant in a carrier gas. The quantity of odorant displaced depends on its vapor pressure and the carrier gas flow. A constant flow of nitrogen, regulated by a flow regulator, carries the odorant from a sample container to a mixing chamber. There, the carrier gas-odor mixture is diluted with odorless air. From the mixing chamber one part of the diluted odorous air is allowed to flow via a fused silica capillary to the sniffing funnel. The flow rate through the capillary, which determines the dosage of odorous air from the mixing chamber into the sniffing funnel, depends on the opening the valve which can be regulated via PC from 1 to 256 ml in binary steps. The final dilution of the odorous air sample occurs in the glass funnel by flushing them permanently with odorless air at a flow rate of 8 lt/min. Forced-choice triangle presentation is achieved by a special automated channel setting device where only one position of a switch the odorant delivering capillary enter in the sniffing funnel, whereas in two other positions the capillary is positioned outside the funnel and where the effluent is sucked away. After each trial the channel setting is changed automatically and in a random order. The concentration is calculated from the odorants vapor pressure and from the dilution ratios that were applied in the olfactometer, assuming that vapor pressure saturation is achieved in the sample generator. As a control the concentration is determined analytically by sampling a known volume from the capillary effluent into a headspace filter and by subsequent gas chromatographic quantitation of the odorant in the desorption solution.

Each panelist (panel of 15 persons) starts sniffing at the olfactometer at a concentration level at which he perceives the odorant at medium intensity. After three correct answers in three consecutive trials (or four correct ones of five trials) at the same level, stimulus concentration is decreased by a factor of two to the next lower level, and so on, until the panelist has reached his threshold level. The final threshold value of a given odorant is obtained as the mean value of all individual threshold levels.

As explained in more detail herein below, the coordinates A and B are complex functions of the amount of ingredient at a source at the time olfactory performance is assessed; of the distance at which the olfactory performance is assessed; and of the dilution taking place between the source and the point of assessment due to convection flows. The amount of ingredient at a source depends on the amount of time perfume has been allowed to evaporate after having been placed on a substrate. It is indeed well known, that once a perfume is deposited on a substrate, its composition will vary in time, as evaporation proceeds. It is also well known that the amount of each ingredient on the substrate will decrease and that the rate of decrease of any given ingredient will be proportional to the vapour pressure of the ingredient.

As used herein, the term "coherent olfactory impact" in relation to a perfume composition is taken to mean that the olfactory impact of all perfume ingredients are perceived within a period of time at some distance from the source such that the olfactory characteristics of the impact will be homogeneous and remain qualitatively unchanged as time evolves. In contrast, a perfume composition exhibits an incoherent olfactory impact when it is characterized by successive smells having different olfactory characteristics. For example, a fragrance composition having an incoherent olfactory impact may develop in a first step a powdery smell, followed by a floral smell and evolving step by step until it becomes perceived as a full perfume.

As used herein a perfume composition exhibiting a "fast developing olfactory impact" is characterised by an olfactory impact that increases sharply with time. A fragrance composition having such sharp olfactory profile may be rapidly noticed at some distance of a source and, provided it has a coherent olfactory impact, it may be immediately recognized.

As used herein, a perfume composition exhibits a "long-lasting olfactory impact" if its olfactory impact remains perceivable over a prolonged period of time, for example for a period of 30 seconds or more at the location the perfume is perceived.

The present disclosure provides a method directed to the characterization of the spatio-temporal attributes of fragrances under controlled conditions. In particular, the method characterises spatio-temporal attributes of fragrances under convection flows having controlled spatial distribution and velocity.

In a particular embodiment the method comprises the steps of:

a) providing a device for generating and emitting a directional air flow,
b) placing a sample of a perfume composition in said device such that it is disposed in the path of the air flow,
c) entraining said perfume composition in the air flow and emitting it from the device as a scented plume in which the perfume composition is substantially confined, and
d) directing the scented plume along a channel towards an aperture in said channel at a defined distance at which aperture the scented plume can be smelled and assessed.

Figure 2:
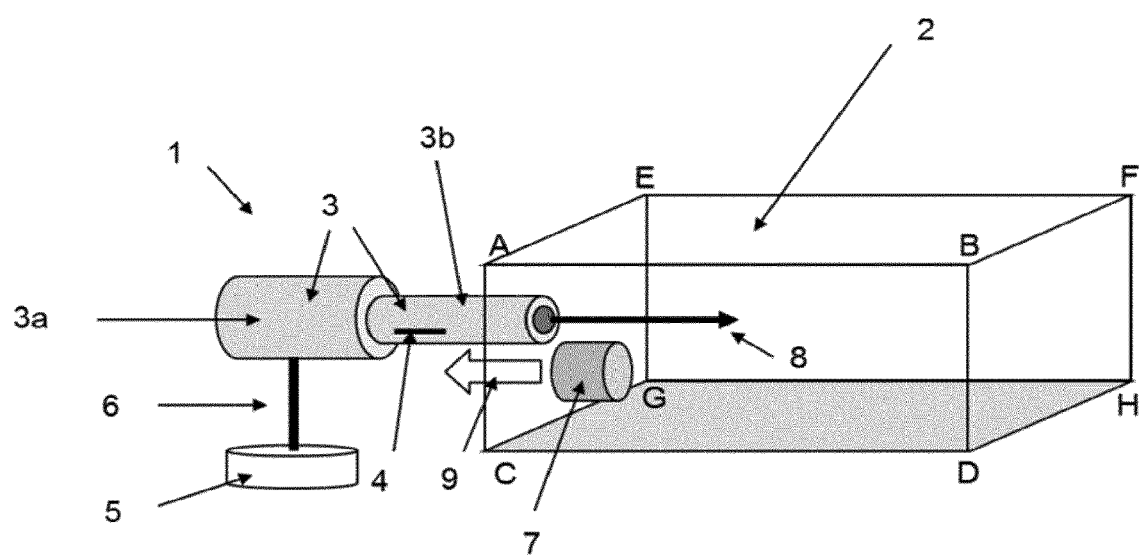
FIG. 2 depicts a device capable of generating and emitting directional air flow, described in more detail hereinafter.

A schematic representation of a device capable of generating and emitting directional air flow is shown in FIG. 2. A device (1) consists of a hollow body (3), comprising a broader part (3a) housing a fan (not shown) for generating an air flow, which can be flushed out of the housing via an elongate conduit (5), hosted in a narrower part (3b) of the body, whereas the direction of the flow is represented schematically by the black arrow (8). The inner diameter of the conduit may be smaller than 10 cm, more preferably smaller than 5 cm and most preferably smaller than 2 cm. The inner diameter of the broader part is not critical, but is preferably between 2 and 5 cm and most preferably between 2.5 and 3.5 cm. Preferably, there is a conical part (not shown on the picture) between the broader part and the narrower part, so that the inner diameter of the hollow body is progressively reduced from the broader part to the narrower part, in order to minimize turbulences in the air flow. The body contains a slot or aperture (4) for receiving a sample of a fragrance composition on a suitable support (not shown), such as a glass plate, paper strip, fabric strip, artificial skin, animal skin, hair and the like. The housing may contain a thermo-regulated element (not shown) for heating the sample. The housing is fixed on a holder (5) by means of an optionally flexible foot (6) allowing orientation of the conduit in all directions of space. In use, the fan generates a directional air flow, which passes over the sample thereby to entrain the fragrance composition and create a fragrance plume that is expressed through the conduit and emitted into a channel (2) that is delimited by panels (ABCD) and (EFGH), which suppress undesirable lateral room convection. The top of the channel (ABEF) must be open to enable an evaluator to assess the fragrance plume at different distances along the channel.

The panels ABCD and EFGH may be parallel or not, although a parallel arrangement is preferred. The segments CD and GH may have equal or different lengths, although equal lengths are preferred, and may be varied, depending on the distance where the olfactory assessment needs to be performed. Typically the length of segments CD and GH is at least 0.5 m, preferably at least 1 m and most preferably at least 1.5 m. The width of the channel, as defined by the length of the segments AE, CG, BF and GH may be at least 0.1 m, preferably at least 0.3 m and most preferably at least 0.5 m. The height of the channels defined by the segment AC, EG, BD and FH may be at least 0.3 m, preferably at least 0.5 m and most preferably at least 0.7 m.

In a specific embodiment of the present disclosure, the device (1) has a length of 20.5 cm and is fixed on a flexible foot having a height of 18 cm and which can be oriented in all direction of the space. The flexible foot is fixed on a holder having a diameter of 11.5 cm and a height of 3.5 cm.

The diameter of the housing (3) is 3.5 cm in the broader part and 2.5 cm in the narrower part (3), the internal diameter of the broader part (3a) is 2.6 cm and the internal diameter of the narrower part (3b) is 1.4 cm. The length of the broader part is 8 cm, including a hollow conical portion having a height of 1 cm (not shown in picture 1), allowing the progressive reduction of the inner diameter from 2.6 to 1.4 cm. The length of the narrower part is 12 cm. The thermo-regulated plate built in the housing has a surface of 5 by 2 $cm^2$. The length of the slit (or sampler port) (4) is 4.1 cm and its width is 0.3 cm. These dimensions are, however, not critical and can be adapted, depending on the needs.

The temperature of the thermo-regulated element may be measured by any known means, such as thermocouple, platinum probe or infra-red detector, while the air flow through the directional tube may be measured, for example, using an anemometer or a Venturi element built up in the tube and connected to a pressure gauge, or any flow sensor.

The amount of fragrance composition deposited on the support is typically from 0.01 to 10 microliters, preferably from 0.05 to 5 microliters, and most preferably from 0.1 to 1.5 microliters. The composition may be deposited as neat oil or diluted in a hydro-alcoholic solvent, or any other suitable solvent.

In a specific embodiment, the support is a glass plate, having a rectangular portion etched or ground, which is surrounded by an un-etched glass frame. The length and width of the etched portion are typically 1.8 cm and 0.4 cm, and the width of the un-etched glass frame is typically 0.1 cm. Hence the surface of the whole glass plate is typically 2 by 0.5 $cm^2$.

The glass plate may be inserted in a sealable sample holder, which is designed in such a way that one part of the holder comprising the glass plate can be inserted into the device (1) through the slit (4), whilst another part remains outside and serves as a gripping means allowing easy sample insertion and removal. The dimensions of the sample holder are commensurate with the size of the slit (4), so that the plug is adjusted in the device in such a way that possible voids between the sample holder and the boundaries of the slit are minimized, e.g. not larger than 0.5 millimetres. The typical dimensions of the sample holder are 5.3 cm×4 cm and the thickness of the part that is introduced in the slit (4) is 0.2 cm. The sample holder can be sealed by any sealing means, so that the evaporation of the perfume deposited on the glass plate is prevented. Typically, the sealing means is removed before insertion in the device (1).

Measurements may be performed on fresh fragrance compositions or after compositions have been allowed to evaporate for a certain time. Preferably, it compositions are left to evaporate for at least 30 minutes, preferably at least one hour and most preferably at least 2 hours, before being inserted in the device (1). A typical evaporation time is 4 hours at a temperature of 32±2° C. Under these conditions, the state of a composition is closer to that applied to a consumer in the day-to-day life and the evaluation provides a better picture of the performance of a fragrance composition under real life conditions. In addition, the evaporation kinetics of compositions will be much slower after 4 hours evaporation time than in the early stage of the evaporation, which makes variations between samples less significant and improves the reproducibility of the evaluation.

The length of the channel may be arbitrarily defined, depending on the distance at which a performance assessment is desired. The evaluation is however performed at a distance larger than 0.5 metres, more preferably at distance larger than 1 m and most preferably larger than 1.5 metres. e.g. 2 metres.

The device and channel may be placed in a room having constant ventilation conditions maintained at constant temperature and humidity. Convection flows in the room should be minimized and the way the air circulates in the room should be held constant, the temperature in the room should not vary by more than ±5° C. over time and the relative humidity in the room should not vary by more than ±20%. Such conditions are easily realized using standard air conditioning systems.

The sample temperature may take any desired value of the thermometric scale and is only limited by the thermal resistance of the materials constituting the device and of the perfume ingredients. Typically, the temperature preferably ranges from 0° C. to 150° C., more preferably from 10° C. to 100° C. and most preferably from 20° C. to 50° C. Temperatures below room temperatures are best achieved by embedding cooling elements in the thermo-regulated plate. A typical sample temperature is 32±2° C.

In another specific embodiment of the present disclosure, the evaluation procedure involves the steps of:—
  (i) allowing a perfume sample evaporating for a certain time T1 in an open environment, at a temperature of from 20 to 35° C., T1 being preferably longer than 30 minutes, more preferably longer than 60 minutes and most preferably at least 120 minutes,
  (ii) Inserting said sample into the device, which has been maintained at a temperature of 32±2° C.
  (iii) evaluating the olfactory characteristics and intensity of the smell at the output of the channel (rectangle BDFH in FIG. 2) as a function of time and
  (iv) after a specific time T2, optionally evaluating the olfactory characteristics and intensity of the smell at different locations on top of the channel (ABEF of FIG. 2), starting from the output and moving downstream, within a time interval T3.

The sample is then removed from the device and the channel is flushed using the fan (7), operating in such a way that the air contained in the channel is moved in the opposite direction relatively to the flow produced by the device, as symbolized by the white arrow (9) in FIG. 2. Once the channel is olfactorily clean, a second evaluation can be initiated.

The convection in the room and the flow rate at the aperture of the conduit (5) are preferably fixed in such a way that:—
  1) 10 microliters of a solution of RADJANOL (2-Ethyl-4-(2,2,3-trimethyl-3-cyclopenten-1-yl)-2-buten-1-ol;2-Ethyl-4-(2',2',3-trimethylcyclopent-3'-enyl)but-2-enol) at 0.24% by weight in a solvent mixture comprising 76.4% ethanol, 10% tri-ethyl citrate and 3.6% water, evaporated for 4 hours under standard room conditions (20±2° C., 50±20% relative humidity) on a glass plate, is detected by more than 90% of panelist assessing the ingredient at the outlet of a 2 meter long channel, as described in FIG. 2, with an average intensity of 4.5±0.5 on a scale of 1-10. This scale may be defined in such a way that an ingredient having a barely noticeable odour strength under the conditions of the measurement will be given an intensity of 1, while an ingredient producing the strongest imaginable smell under the conditions of the measurement will be given an intensity of 10. The scale is furthermore calibrated by assigning a note of 6 to CYCLOHEXAL-(4-(4-hydroxy-4-methylpentyl)cyclohex-3-ene carbaldehyde)—which is used herein as benchmark; and
  2) 10 microliters of a solution of POLYSANTOL ((E)-3,3-dimethyl-5-(2,2,3-trimethyl-3-cyclopenten-1-yl)-4-penten-2-ol) at 0.24% by weight in a solvent mixture comprising 76.4% ethanol, 10% tri-ethyl citrate and 3.6% water, evaporated for 4 hours under standard room conditions (20±2° C., 50±20% relative humidity) on aforementioned glass plate, can be detected by up to 70% of the panelist at the outlet of a 2 meter long channel, as described in FIG. 2, with an average intensity of 1±0.5 on a scale of 10.

The skilled person will appreciate that the aforementioned conditions and experimental set-up design constitute merely an example of how one can determine the measurement of trail. In any event, these conditions are taken to be met when the room convection is minimized during the measurement, e.g. by shutting down any air control system in the room, and applying a flow of 5 to 30 ml/min at the aperture of the narrower part (3*b*) in FIG. 2 wherein the exact value of the flow is to be set by the operator.

The assessment of the olfactory attributes at distance from a source may be diverse and comprise olfactory intensity or impact, and more descriptive qualifiers, such as odour description, sharpness, transparency, presence, volume and the like. Such qualifiers determine the "nature" of the olfactory profile, as discussed in more detail hereunder.

By "odour descriptors" is meant a description of the smell in words according to a specific vocabulary, usually defined by convention. A suitable odour descriptor vocabulary comprises, but is not limited to terms such as "citrus", "rosy", "hesperidic", "green", "woody", "ambry", "musky", and the like. Odour descriptors are widely used in the art of assessing perfumery and a more detailed discussion is not merited herein. A full discussion of odour descriptors is provided in "Perfume and Flavour Chemicals", S. Arctander, Allured Publishing Corporation, 1994, IL, USA, which is incorporated herein by reference.

The present method enables one to assess the trail performance of perfumes. Typically, the perfume is applied onto a substrate at a concentration of 10% by weight in a solvent, such as ethanol, ethanol/water mixture, propylene glycol, dipropylene glycol, triethyl citrate and the like, or as provided by vendors, for example 5%, 10% or 15% by weight. Typically, 10 microliters of perfume solution is applied on the substrate.

The present method also enables one to group perfume ingredients that behave coherently with respect to each other, by which is meant, groupings of perfume ingredients can be made based on the observation that they are detected at a particular defined point in space relative to a perfume source within a given time frame, such that they display a coherent olfactory impact, as this term is defined above.

A first grouping of perfume ingredients, referred to hereafter as INGREDIENT GROUP 1, is selected from those ingredients having a combination of standard equilibrium headspace concentration and odour detection threshold such that said ingredients lie on or below a Distance Perception Boundary Line (DPBL) in a log $HS_i^0$ vs. log $ODT_i$ plot, characterized by a coordinate A=[log($ODT_a$); log($HS_a$)]=[−3;6] and B=[log ($ODT_b$);log ($HS_b$)]=[2;1]; wherein $ODT_i$ is the odour detection threshold of a perfume ingredient i, measured in nanograms/litre; and $HS_i$ is the equilibrium headspace concentration of ingredient i, measured in micrograms/litre; and wherein the term "log" refers to the decimal logarithm.

When 10 microliters of a solution of 0.24% by weight of an INGREDIENT GROUP 1 material in a solvent mixture comprising 76.4% ethanol, 10% tri-ethyl citrate and 3.6% water is placed on a substrate, such as an etched glass surface, and left for 30 minutes at a temperature of 25° C. before being placed at a temperature of 32+/−2° C., under aforementioned flow and room convection conditions, it will be detectable 2 metres downstream of the substrate within a detection time of 5 to 120 seconds on average and with an average intensity larger than 1 on a scale of 10, as defined above.

Perfume ingredients of INGREDIENT GROUP I include but are not limited to (2-benzyl-1,3-dioxolan-4-yl)methanol; (2-(1-propoxyethoxy)ethyl)benzene; 1-(4-methoxyphenyl) ethanone; allyl 2-phenoxyacetate; (Z)-4,11,11-trimethyl-8-methylenebicyclo[7.2.0]undec-4-ene; (E)-2-methoxy-4-(prop-1-en-1-yl)phenyl acetate; 1-(pyrazin-2-yl) ethanone; 4-formyl-2-methoxyphenyl acetate; 2,6,10-trimethylundec-9-enal; undecanal; decanal; dodecanal; 2-methylundecanal; tridecanal; (E)-undec-9-enal; 4-[(6,6-dimethyl-5-bicyclo[2.2.1]heptanyl)methyl]-2-methylcyclohexan-1-one; allyl 2-(isopentyloxy)acetate; allyl 3-cyclohexylpropanoate; 1-((2-(tert-butyl)cyclohexyl)oxy)butan-2-ol; 3,8,8,11a-tetramethyldodecahydro-1H-3,5a-epoxynaphtho[2,1-c] oxepine; (2,4a,5,8a-tetramethyl-1,2,3,4,7,8-hexahydronaphthalen-1-yl) formate; (Z)-oxacycloheptadec-10-en-2-one; 2,5,5-trimethyl-1,2,3,4,4a,5,6,7-octahydronaphthalen-2-ol; (4aR,5R,7aS,9R)-octahydro-2,2,5,8,8,9a-hexamethyl-4h-4a,9-methanoazuleno(5,6-d)-1,3-dioxole; 3a,6,6,9a-tetramethyldodecahydronaphtho[2,1-b]furan; 3a,6,6,9a-tetramethyldodecahydronaphtho[2,1-b]furan; (Z)-2-benzylideneheptanal; pentyl 2-phenylacetate; pentyl 2-hydroxybenzoate; (4-methoxyphenyl)methanol; 1-phenylethanethiol; 4-methoxybenzaldehyde; (E)-methyl 2-((7-hydroxy-3,7-dimethyloctylidene)amino)benzoate; 7-isopentyl-2H-benzo[b][1,4]dioxepin-3(4H)-one; (1R,2S,4R)-2'-isopropyl-1,7,7-trimethylspiro[bicyclo[2.2.1]heptane-2,4'-[1,3]dioxane]; benzophenone; benzyl benzoate; benzyl (E)-3-phenylprop-2-enoate; benzyl 2-phenylacetate; benzyl 2-hydroxybenzoate; octahydro-2H-chromen-2-one; (ethoxymethoxy)cyclododecane; 3-(4-(tert-butyl)phenyl) propanal; (1R,5S,E)-1,5-dimethylbicyclo[3.2.1]octan-8-one oxime; 6-(sec-butyl)quinoline; 7-methyl-2H-benzo[b][1,4] dioxepin-3(4H)-one; octanal, 6-methoxy-2,6-dimethyl-; 3-(4-methoxyphenyl)-2-methylpropanal; 3-hydroxy-4,5-dimethylfuran-2(5H)-one; 5-isopropyl-2-methylphenol; 2-methyl-5-(prop-1-en-2-yl)cyclohex-2-enone; 1,1,2,3,3-pentamethyl-2,3,6,7-tetrahydro-1H-inden-4 (5H)-one; 4-(1,3-benzodioxol-5-yl)butan-2-one; ((1S,8aR)-1,4,4-trimethyl-2,3,3a,4,5,8-hexahydro-1H-5,8a-methanoazulen-6-yl) methanol; (1S,6R,8aR)-1,4,4,6-tetramethyloctahydro-1H-5, 8a-methanoazulen-6-yl acetate; (1S,6R,8aR)-1,4,4,6-tetramethyloctahydro-1H-5,8a-methanoazulen-6-ol; (4Z, 8Z)-1,5,9-trimethyl-13-oxabicyclo[10.1.0]trideca-4,8-diene; (1R,6S,8aS)-6-methoxy-1,4,4,6-tetramethyloctahydro-1H-5,8a-methanoazulene; methyl 2-(3-oxo-2-pentylcyclopentyl)acetate; 3a,6,6,9a-tetramethyldodecahydronaphtho[2,1-b]furan; (E)-1-(2,6,6-trimethylcyclohex-2-en-1-yl)hepta-1,6-dien-3-one; 3-phenylprop-2-enoic acid; (E)-3-phenylprop-2-en-1-ol; 3-phenylpropenal; 3-(4-acetyloxyphenyl)prop-2-enoic acid; 3-phenylprop-2-enyl 3-phenylprop-2-enoate; [(Z)-hex-3-enyl]2-aminobenzoate; (Z)-hex-3-en-1-yl 2-hydroxybenzoate; 3,7-dimethyl-oct-6-en-1-ol; 3,7-dimethyloct-6-en-1-yl ethyl oxalate; 2-((3,7-dimethyloct-6-en-1-yl)oxy)acetaldehyde; (Z)-cycloheptadec-9-enone; dodecanenitrile; 2-(2-mercaptopropan-2-yl)-5-methylcyclohexanone; 2-(3-phenylpropyl)pyridine; 2-hydroxy-3-methylcyclopent-2-enone; (Z)-3-methylcyclotetradec-5-enone; 2H-chromen-2-one; 2-methoxy-4-methylphenol; p-cresol; p-tolyl acetate; p-tolyl octanoate; p-tolyl 2-phenylacetate; 4-isopropylbenzonitrile; 3-(4-isopropylphenyl)-2-methylpropanal; allyl 2-(cyclohexyloxy)acetate; 4-(4-hydroxy-4-methylpentyl)cyclohex-3-enecarbaldehyde; cyclohexyl 2-hydroxybenzoate; 3-(4-methylcyclohex-3-en-1-yl)butan-1-ol; 8,8-dimethyl-1,2,3,4,5,6,7,8-octahydronaphthalene-2-carbaldehyde; (E)-1-(2,6,6-trimethylcyclohexa-1,3-dien-1-yl)but-2-en-1-one; (E)-1-(2,6,6-trimethylcyclohex-2-en-1-yl)but-2-en-1-one; (E)-1-(2,6,6-trimethylcyclohex-1-en-1-yl)but-2-en-1-one; (E)-1-(2,6,6-trimethylcyclohex-3-en-1-yl)but-2-en-1-one; 6-pentyltetrahydro-2H-pyran-2-one; 6-hexyltetrahydro-2H-pyran-2-one; 6-heptyltetrahydro-2H-pyran-2-one; 6-propytetrahydro-2H-pyran-2-one; 6-propytetrahydro-2H-pyran-2-one; 5-octyldihydrofuran-2(3H)-one; (E)-dec-2-enal; (E)-dec-4-enal; decanal; 2-(sec-butyl)-1-vinylcyclohexyl acetate; 1-oxacycloheptadecan-2-one; 1-methoxy-4-propylbenzene; 2-methoxy-4-propylphenol; (Z)-3,7,11-trimethyldodeca-6,10-dienal; 4-(2,6,6-trimethylcyclohex-1-en-1-yl) butan-2-one; 2-N-hexyl-3-methoxycarbonylcyclopentanone; 3-methyl-2-pentylcyclopent-2-enone; methyl 2-(methylamino)benzoate; 2-(2-(3,3,5-trimethylcyclohexyl)acetyl)cyclopentanone; 7,9-dimethylspiro[5.5]undecan-3-one; 6-heptyltetrahydro-2H-pyran-2-one; 5-octyldihydrofuran-2(3H)-one; (E)-dodec-2-enal; (E)-4-((3aS,7aS)-hexahydro-1H-4,7-methanoinden-5(6H)-ylidene)butanal; (E)-3-methyl-5-(2,2,3-trimethylcyclopent-3-en-1-yl)pent-4-en-2-ol; ethyl (E)-3-phenylprop-2-enoate; 8-ethyl-1-oxaspiro[4.5]decan-2-one; 2-ethyl-3-hydroxy-4H-pyran-4-one; ethyl 2-phenylacetate; ethyl 3-phenyloxirane-2-carboxylate; ethyl 2,6,6-trimethylcyclohexa-1,3-diene-1-carboxylate; 3-ethoxy-4-hydroxybenzaldehyde; 1,4-dioxacycloheptadecane-5,17-dione; 4-allyl-2-methoxyphenol; 4-allyl-2-methoxyphenyl acetate;

methyl 2,4-dihydroxy-3,6-dimethylbenzoate; (4Z)-cyclopentadec-4-en-1-one; 3-(4-methoxyphenyl)-2-methylpropanal; 3a,6,6,9a-tetramethyldodecahydronaphtho[2,1-b]furan; 1-(3,5,5,6,8,8-hexamethyl-5,6,7,8-tetrahydronaphthalen-2-yl)ethanone; 3-(3-isopropylphenyl)butanal; (E)-undec-9-enenitrile; (3aR,6S,7aS)-3a,4,5,6,7,7a-hexahydro-1H-4,7-methanoinden-6-yl propionate; 2,4,6-trimethyl-4-phenyl-1,3-dioxane; (Z)-1-(cyclooct-3-en-1-yl)propan-1-ol; methyloct-2-ynoate; 3-methyldodecanenitrile; (3aS,4S,7R,7aS)-ethyl octahydro-1H-4,7-methanoindene-3a-carboxylate; 4,6,6,7,8,8-hexamethyl-1,3,4,6,7,8-hexahydrocyclopenta[g]isochromene; 1-(3,3-dimethylcyclohex-1-en-1-yl)pent-4-en-1-one; N,2-dimethyl-N-phenylbutanamide; (3aR,6S,7aS)-3a,4,5,6,7,7a-hexahydro-1H-4,7-methanoinden-6-yl isobutyrate; 1-(1,2,8,8-tetramethyl-1,2,3,4,5,6,7,8-octahydronaphthalen-2-yl)ethanone; (E)-3,7-dimethylocta-2,6-dien-1-ol; (E)-6,10-dimethylundeca-5,9-dien-2-one; (E)-3,7-dimethylocta-2,6-dien-1-yl 2-phenylacetate; (E)-(E)-3,7-dimethylocta-2,6-dien-1-yl 2-methylbut-2-enoate; 3a-ethyl-6,6,9a-trimethyldodecahydronaphtho[1,2-c]furan; 2-(3,8-dimethyl-1,2,3,4,5,6,7,8-octahydroazulen-5-yl)propan-2-yl acetate; (E)-oxacyclohexadec-12-en-2-one; methyl 2-(3-oxo-2-pentylcyclopentyl)acetate; methyl 2-(3-oxo-2-pentylcyclopentyl)acetate; benzo[d][1,3]dioxole-5-carbaldehyde; 2-(1-(3,3-dimethylcyclohexyl)ethoxy)-2-methylpropyl propionate; heptyl-2-cyclopentanone; (Z)—(Z)-hex-3-en-1-yl hex-3-enoate; (Z)-hex-3-en-1-ol; (Z)-hex-3-en-1-yl 2-hydroxybenzoate; hexyl benzoate; hexyl (E)-3-phenylprop-2-enoate; (E)-2-benzylideneoctanal; hexyl 2-hydroxybenzoate; 2-ethyl-4-hydroxy-5-methylfuran-3(2H)-one; 7-hydroxy-3,7-dimethyloctanal; 1H-indole; 8,8-di(1H-indol-3-yl)-2,6-dimethyloctan-2-ol; (E)-4-(2,6,6-trimethylcyclohex-1-en-1-yl)but-3-en-2-one; (E)-3-methyl-4-(2,6,6-trimethylcyclohex-2-en-1-yl)but-3-en-2-one; (E)-4-(2,6,6-trimethylcyclohex-2-en-1-yl)but-3-en-2-one; (E)-4-(2,5,6,6-tetramethylcyclohex-2-en-1-yl)but-3-en-2-one; (E)-4-(2,5,6,6-tetramethylcyclohex-2-en-1-yl)but-3-en-2-one; 1-(2,3,8,8-tetramethyl-1,2,3,4,5,6,7,8-octahydronaphthalen-2-yl)ethanone; 4-formyl-2-methoxyphenyl isobutyrate; 2-isobutylquinoline; (2-methoxy-4-prop-1-enylphenyl) acetate; (E)-2-methoxy-4-(prop-1-en-1-yl)phenol; 6-isopropylquinoline; (E)-1-(2,6,6-trimethylcyclohex-2-en-1-yl)pent-1-en-3-one; (E)-3-methyl-4-(2,6,6-trimethylcyclohex-2-en-1-yl)but-3-en-2-one; (E)-3-methyl-4-(2,6,6-trimethyl cyclohex-2-en-1-yl)but-3-en-2-one; (E)-3-methyl-4-(2,6,6-trimethyl cyclo hex-2-en-1-yl)but-3-en-2-one; 2-hexylcyclopent-2-en-1-one; (3aR,6S,7 aS)-3a,4,5,6,7,7a-hexahydro-1H-4,7-methanoinden-6-yl acetate; (Z)-6-(pent-2-en-1-yl)tetrahydro-2H-pyran-2-one; (Z)-5-(hex-3-en-1-yl)-5-methyldihydrofuran-2(3H)-one; (E)-6-(pent-3-en-1-yl)tetrahydro-2H-pyran-2-one; (Z)-3-methyl-2-(pent-2-en-1-yl)cyclopent-2-enone; (1-methyl-2-((1,2,2-trimethylbicyclo[3.1.0]hexan-3-yl) methyl)cyclopropyl)methanol; 5-(sec-butyl)-2-(2,4-dimethyl cyclohex-3-en-1-yl)-5-methyl-1,3-dioxane; Benzoic acid, 2-hydroxy-, (3Z)-1-methyl-3-hexen-1-yl ester; 4-(1-ethoxyvinyl)-3,3,5,5-tetramethylcyclohexanone; (E)-2,4,4,7-tetramethylnona-6,8-dien-3-one; 6,8-Nonadien-3-one, 2,4,4,7-tetramethyl-, oxime; 2,8,8-trimethyloctahydro-1H-4a,2-(epoxymethano)naphthalen-10-one; 8-isopropyl-1-oxaspiro[4.5]decan-2-one; (2E,6Z)-3,7-dimethylnona-2,6-dienenitrile; (E)-methyl 2-(((2,4-dimethylcyclohex-3-en-1-yl)methyl ene)amino)benzoate; 3-(4-(tert-butyl)phenyl)-2-methylpropanal; 3,7-dimethylocta-1,6-di en-3-yl cinnamate; 5-Methyl-7-(1-methyl ethyl)bicyclo[2.2.2]oct-5-ene-2-carboxaldehyde; 2,4-dimethyl-4,4a,5,9b-tetrahydroindeno[1,2-d][1,3]dioxine; 2,2-dimethyl-3-(m-tolyl)propan-1-ol; 2-methyl-4-oxo-4H-pyran-3-yl isobutyrate; 3-hydroxy-2-methyl-4H-pyran-4-one; 2-(4-(tert-butyl)phenyl)acetonitrile; 3-methyl-5-phenylpentanal; 3-methyl-5-phenylpentanol; 4-(4-methoxyphenyl)butan-2-one; methyl 2-amino benzoate; methyl-(E)-3-phenylprop-2-enoate; methyl 2-hydroxy-5-methylbenzoate; 5-hexyl-5-methyldihydrofuran-2(3H)-one; 2-ethoxy-4-(methoxymethyl)phenol; 2-methoxy-1,1'-biphenyl; (Z)-methyl 2-(3-oxo-2-(pent-2-en-1-yl)cyclopentyl)acetate; 4,4,8a-trimethyldecahydronaphthalen-4a-ol; 3-Butenal, 2,3-dimethyl-4-(2,6,6-trimethyl-2-cyclohexen-1-yl)-; (E)-1,2-dimethoxy-4-(prop-1-en-1-yl)benzene; 8-methyl-1-oxaspiro[4.5]decan-2-one; (9E,12E)-methyl octadeca-9,12-dienoate; methyl non-2-ynoate; methyl 2-phenylacetate; 4-methyl-5-pentyldihydrofuran-2(3H)-one; Dec-5 (6)-enoic acid (E/Z); Naphth[2,3-b]oxirene, 1a,2,3,4,5,6,7,7a-octahydro-1a,3,3,4,6,6-hexamethyl-, (1aR,4S,7 aS)-rel-; (Z)-3-methylcyclopentadec-5-enone; 3-methylcyclopentadecanone; 1,4-dioxacyclohexadecane-5,16-di one; Cyclopentadecanone; 1-(4-(tert-butyl)-2,6-dimethyl-3,5-dinitrophenyl)ethanone; 1,7-dioxacycloheptadecan-8-one; benzene, 1-(1,1-dimethylethyl)-3,5-dimethyl-2,4,6-trinitro-; 4-(4-methylpent-3-en-1-yl)cyclohex-3-enecarbaldehyde; (4-(4-methylpent-3-en-1-yl)cyclohex-3-en-1-yl)methyl acetate; 2-methylundecanoic acid; (3,3,4,5-Pentamethyl-11,13-dioxatricyclo-[7,4,0,0-{2,6}]-tridec-2/6-ene); 2-(2-(4-methylcyclohex-3-en-1-yl)propyl)cyclopentanone; (Z)-3,7,11-trimethyldodeca-1,6,10-trien-3-yl acetate; 2-ethoxynaphthalene; 1-(3-methylbenzofuran-2-yl)ethanone; (E)-13-methyloxacyclopentadec-10-en-2-one; (2E,6Z)-nona-2,6-dienal; (2E,6Z)-nona-2,6-dien-1-ol; (Z)-non-6-enal; (Z)-non-6-en-1-ol; 4,4a-dimethyl-6-(prop-1-en-2-yl)-4,4a,5,6,7,8-hexahydronaphthalen-2(3H)-one; 6-propyltetrahydro-2H-pyran-2-one; 5-butyldihydrofuran-2(3H)-one; 2,4-dimethyl-2-(5,5,8,8-tetramethyl-5,6,7,8-tetrahydronaphthalen-2-yl)-1,3-dioxolane; 1-naphthalen-2-ylethanone; 3-methoxy-5-methylphenol; 2-methyl-4-propyl-1,3-oxathiane; p-tolyl octanoate; p-tolyl isobutyrate; p-tolyl 2-phenylacetate; 2-ethyl-N-methyl-N-(m-tolyl)butanamide; (1-methyl-2-(((1R,3R)-2,2,3-trimethylcyclopentyl)methyl) cyclopropyl)methanol; 4,8a,9,9-tetramethyldecahydro-1,6-methanonaphthalen-1-ol; 5-heptyldihydrofuran-2(3H)-one; 2-methyl-4-methylene-6-phenyltetrahydro-2H-pyran; 2-cyclohexylidene-2-phenylacetonitrile; 3,7-dimethylocta-1,6-dien-3-yl dimethylcarbamate; Benzeneacetonitrile, alpha-cyclohexylidene-6-methyl-; 1-(1,1,2,3,3,6-hexamethyl-2H-inden-5-yl)ethanone; 2-cyclohexylhepta-1,6-dien-3-one; 2-phenoxyethyl isobutyrate; 2-phenoxyacetaldehyde; 2-phenylacetic acid; phenethyl acetate; 2-phenylethanol; phenyl-(E)-3-phenylprop-2-enoate; phenethyl 2-phenylacetate; phenethyl 2-hydroxybenzoate; 3-phenylpropanal; 3-phenylpropan-1-ol; 3-(6,6-dimethylbicyclo[3.1.1]hept-2-en-2-yl) propanal; (3aR,6S,7aS)-3a,4,5,6,7,7a-hexahydro-1H-4,7-methanoinden-6-yl pivalate; (E)-3,3-dimethyl-5-(2,2,3-trimethyl-3-cyclopenten-1-yl)-4-penten-2-ol; (2E,5E)-5,6,7-trimethylocta-2,5-dien-4-one; (1S,4R,6S)-4,7,7-trimethyl-4-(3-methylbut-2-en-1-yl)bicyclo[4.1.0]heptan-3-one; 1-methyl-4-(4-methylpent-3-en-1-yl)cyclohex-3-enecarbaldehyde; 2-ethoxy-4-(isopropoxymethyl)phenol; 5-pentyldihydrofuran-2(3H)-one; 6-(sec-butyl)quinoline; (E)-2-ethyl-4-(2,2,3-trimethylcyclopent-3-en-1-yl)but-2-en-1-ol; (E)-2-ethyl-4-(2,2,3-trimethylcyclopent-3-en-1-yl)but-2-en-1-ol; 4-(4-hydroxyphenyl)butan-2-one; 2,4-dimethyl-4-phenyltetrahydrofuran; (2R,8aS)-3',6-dimethyl-3,4,4a,5,8,8a-hexahydro-1H-spiro[1,4-methanonaphthalene-2,2'-oxirane]; acetic acid (1-oxopropoxy)-, 1-(3,3-dimethyl cyclohexyl)ethyl ester; 2,2,2-trichloro-1-phenylethyl acetate; dec-9-en-1-ol; 2-methyl-5-phenylpentan-1-ol;

3-isobutyl-1-methylcyclohexanol; 4-methylene-2-phenyltetrahydro-2H-pyran; (3S,5R,8S)-5-Isopropenyl-3,8-dimethyl-3,4,5,6,7,8-hexahydro-1(2H)-azulenone; 2,6,6-trimethylcyclohexa-1,3-dienecarbaldehyde; 2,3,3-trimethyl-2,3-dihydro-1H-inden-1-one; 3-methyl-5-(2,2,3-trimethylcyclopent-3-en-1-yl)pentan-2-ol; 3-((1R,2S,4R,6R)-5,5,6-trimethylbicyclo[2.2.1]heptan-2-yl)cyclohexanol; (E)-2-methyl-4-(2,2,3-trimethyl-1-cyclopent-3-enyl)but-2-en-1-ol; (3aR,4R,6S,7R,7aR)-6-methoxyoctahydro-1H-4,7-methanoindene-1-carbaldehyde; methyl 2,4-dihydroxy-3-methylbenzoate; 2-(1-(3,3-dimethylcyclohexyl)ethoxy)-2-methylpropyl cyclopropanecarboxylate; 3-(4-isobutylphenyl)-2-methylpropanal; 3-methyl-1H-indole; 2',2',3,7,7-pentamethylspiro[bicyclo[4.1.0]heptane-2,5'-[1,3]dioxane]; SPIROGALBANONE 10%/DPG; ethyl-3-methylé-3-phenyloxirane-2-carboxylate; (E)-6-ethyl-3-methyloct-6-en-1-ol; (E)-2-((3,5-dimethylhex-3-en-2-yl)oxy)-2-methylpropyl cyclopropanecarboxylate; (E)-6,10-dimethylundeca-5,9-dien-2-yl acetate; oxacyclohexadecan-2-one; (E)-3,7-dimethylocta-2,6-diene-1-thiol; 2-isopropyl-5-methylphenol; 1-(2,2,6-trimethylcyclohexyl)hexan-3-ol; 1-(cyclopropylmethyl)-4-methoxybenzene; 4-oxo-4-[(2S,3S)-1,1,2,6-tetramethyl-3-(propan-2-yl)-2,3-dihydro-1H-inden-5-yl]butanoic acid; (E)-tridec-2-enenitrile; 3-phenylbutanal; 1-((2E,5Z,9Z)-2,7,8-trimethylcyclododeca-2,5,9-trien-1-yl)ethanone; decahydro-2,6,6,7,8,8-hexamethyl-2h-indeno(4,5-b)furan; 3-(benzo[d][1,3]dioxol-5-yl)-2-methylpropanal; 2-ethoxy-4-methylphenol; 6-hexyltetrahydro-2H-pyran-2-one; (3E,5Z)-undeca-1,3,5-triene; (E)-4-methyldec-3-en-5-ol; (E)-undec-2-enenitrile; 4-hydroxy-3-methoxybenzaldehyde; (E)-2-ethoxy-5-(prop-1-en-1-yl)phenol; (Z)-cyclohexadec-5-enone; (E)-methyl 2-((3-(4-(tert-butyl)phenyl)-2-methylprop-1-en-1-yl)amino)benzoate; 1-((1S,8aS)-1,4,4,6-tetramethyl-2,3,3a,4,5,8-hexahydro-1H-5,8a-methanoazulen-7-yl)ethanone; 2,4-diethoxy-5-methylpyrimidine; 4-methyl-4-phenylpentan-2-yl acetate; (5R,6R)-6,10-dimethyl-3-propan-2-ylidenespiro[4.5]dec-9-en-8-ol; (2R,5R,8S)-4,4,8-trimethyltricyclo[6.3.1.02,5]dodecan-1-yl acetate; (2E,6Z)-nona-2,6-dienenitrile; undec-10-enenitrile; 2-methoxynaphthalene; 2-(2,4-dimethylcyclohexyl)pyridine; Patchouli oil; (E)-9-hydroxy-5,9-dimethyldec-4-enal; 3-(4-isobutyl-2-methylphenyl)propanal, 2-(2-(4-methylcyclohex-3-en-1-yl)allyl)cyclopentanone; 1-((1S,4R,8R)-1,8-dimethyl-2-oxabicyclo[2.2.2]octan-5-yl)ethanol; ((1S,4R,7S)-3,6,7-trimethyl-2-oxabicyclo[2.2.2]octan-5-yl)methanol; 9-hydroxy-5,9-dimethyldecanal; (S)-2-((2S,4aR)-1,1,5,5-tetramethyl-2,3,4,5,6,7-hexahydro-1H-2,4a-methanonaphthalen-8-yl)butan-1-ol; (R)-2-((2S,4aS,8 aS)-1,1,5,5-tetramethyl-2,3,4,5,6,8a-hexahydro-1H-2,4a-methanonaphthalen-8-yl)butan-1-ol; (3aR,5aS,8S,9aR,9bS)-2,2,3a,5,5,9,9-heptamethyloctahydro-3aH-5a,8-methanonaphtho[1,2-d][1,3]dioxole; (1-methyl-2-(5-methylhex-4-en-2-yl)cyclopropyl)methanol; (E)-7-(4-methylpent-1-en-1-yl)-2H-benzo[b][1,4]dioxepin-3(4H)-one.

Perfume ingredients conforming to this definition are deemed to be coherent relative to each other according to how that term is understood in the present invention.

A second grouping of perfume ingredients, referred to hereafter as INGREDIENT GROUP 2 is selected from those ingredients having a combination of standard equilibrium headspace concentration and odour detection threshold such that said ingredients lie on or below a distance perception boundary line in a log $HS_i^0$ vs. log $ODT_i$ plot, characterized by a coordinate $A=[\log(ODT_a);\log(HS_a)]=[-3;6]$ and $B=[\log(ODT_b);\log(HS_b)]=[1;0]$; wherein $ODT_i$ is the odour detection threshold of a perfume ingredient i, measured in nanograms/litre; and $HS_i$ is the equilibrium headspace concentration of ingredient i, measured in micrograms/litre; and wherein the term "log" refers to the decimal logarithm.

When 10 microliters of a solution of 0.24% by weight of said INGREDIENT GROUP 2 ingredient in a solvent mixture comprising 76.4% ethanol, 10% tri-ethyl citrate and 3.6% water is placed on an etched glass plate and left for 4 hours at a temperature of 32+/−2 degree centigrade before being placed at a temperature of 32 degrees centigrade+/−2° C. under aforementioned flow and room convection conditions, this ingredient will be detectable 2 metres downstream of the substrate within a detection time of 5 to 60 seconds on average and with an average intensity larger than 1 on a scale of 10, as defined above.

INGREDIENT GROUP 2 perfume ingredients include: allyl 2-phenoxyacetate; (E)-2-methoxy-4-(prop-1-en-1-yl) phenyl acetate; 1-(pyrazin-2-yl)ethanone; 2-methylundecanal; tridecanal; 4-[(6,6-dimethyl-5-bicyclo[2.2.1]heptanyl) methyl]-2-methyl cyclohexan-1-one; 3,8,8,11a-tetramethyl do decahydro-1H-3,5a-epoxynaphtho[2,1-c]oxepine; 4-formyl-2-methoxyphenyl acetate; (2,4a,5,8a-tetramethyl-1,2,3,4,7,8-hexahydronaphthalen-1-yl) formate; (Z)-oxacycloheptadec-10-en-2-one; 2,5,5-trimethyl-1,2,3,4,4a,5,6,7-octahydronaphthalen-2-ol; (4aR,5R,7 aS,9R)-octahydro-2,2,5,8,8,9a-hexamethyl-4h-4a, 9-methano azuleno (5,6-d)-1,3-dioxole; 3a,6,6,9a-tetramethyl do decahydronaphtho[2,1-b]furan; 3a,6,6,9a-tetramethyldodecahydronaphtho[2,1-b]furan; (4-methoxyphenyl)methanol; 4-methoxybenzaldehyde; (E)-methyl 2-((7-hydroxy-3,7-dimethyloctylidene)amino)benzoate; 7-isopentyl-2H-benzo[b][1,4]dioxepin-3 (4H)-one; benzyl (E)-3-phenylprop-2-enoate; benzyl 2-hydroxybenzoate; octahydro-2H-chromen-2-one; (ethoxymethoxy)cyclododecane; 3-(4-(tert-butyl) phenyl)propanal; 6-(sec-butyl)quinoline; 7-methyl-2H-benzo[b][1,4]dioxepin-3(4H)-one; 3-hydroxy-4,5-dimethylfuran-2(5H)-one; 4-(1,3-benzodioxol-5-yl)butan-2-one; 3a,6,6,9a-tetramethyldodecahydronaphtho[2,1-b]furan; 3-phenylpropenal; (E)-3-phenylprop-2-en-1-ol; [(Z)-hex-3-enyl]2-aminobenzoate; (Z)-hex-3-en-1-yl 2-hydroxybenzoate; (Z)-cycloheptadec-9-enone; 2-(2-mercaptopropan-2-yl)-5-methylcyclohexanone; 2-(3-phenylpropyl)pyridine; (Z)-3-methylcyclotetradec-5-enone; 2H-chromen-2-one; p-tolyl octanoate; ally 2-(cyclohexyloxy)acetate; 4-(4-hydroxy-4-methylpentyl)cyclohex-3-enecarbaldehyde; (E)-1-(2,6,6-trimethylcyclohexa-1,3-dien-1-yl)but-2-en-1-one; (E)-1-(2,6,6-trimethylcyclohex-1-en-1-yl)but-2-en-1-one; (E)-1-(2,6,6-trimethylcyclohex-3-en-1-yl)but-2-en-1-one; 6-pentyltetrahydro-2H-pyran-2-one; 6-hexyltetrahydro-2H-pyran-2-one; 6-heptyltetrahydro-2H-pyran-2-one; (E)-dec-4-enal; 2-(sec-butyl)-1-vinylcyclohexyl acetate; 2-methoxy-4-propylphenol; 2-(2-(3,3,5-trimethylcyclohexyl)acetyl)cyclopentanone; (E)-4-((3aS,7aS)-hexahydro-1H-4,7-methanoinden-5(6H)-ylidene)butanal; (E)-3-methyl-5-(2,2,3-trimethylcyclopent-3-en-1-yl)pent-4-en-2-ol; 8-ethyl-1-oxaspiro[4.5]decan-2-one; 2-ethyl-3-hydroxy-4H-pyran-4-one; (1S,6R,8aR)-1,4,4,6-tetramethyloctahydro-1H-5,8a-methanoazulen-6-ol; 3-ethoxy-4-hydroxybenzaldehyde; 1,4-dioxacycloheptadecane-5,17-dione; 4-allyl-2-methoxyphenol; methyl 2,4-dihydroxy-3,6-dimethylbenzoate; 3-(4-methoxyphenyl)-2-methylpropanal; 3-phenylprop-2-enoic acid; 1-(3,5,5,6,8,8-hexamethyl-5,6,7,8-tetrahydronaphthalen-2-yl)ethanone; 3-(3-isopropylphenyl)butanal; 4,6,6,7,8,8-hexamethyl-1,3,4,6,7,8-hexahydrocyclopenta[g]isochromene; p-tolyl 2-phenylacetate; 1-(3,3-dimethylcyclohex-1-en-1-yl)pent-4-en-1-one; 5-butyldihydrofuran-2(3H)-one; 6-propytetrahydro-2H- pyran-2-one; 5-octyldihydrofuran-2(3H)-one; 1-(1,2,8,8-tetramethyl-1,2,3,4,5,6,7,8-octahydronaphthalen-2-yl)ethanone; 3a-ethyl-6,6,9a-trimethyldodecahydronaphtho[1,2-c]furan; (E)-oxacyclohexadec-12-en-2-one; methyl 2-(3-oxo-2-pentylcyclopentyl)acetate; 1H-indole; (4-(4-methylpent-3-en-1-yl)cyclohex-3-en-1-yl)methyl acetate 2-(1-(3,3-dimethylcyclohexyl)ethoxy)-2-methylpropyl propionate; (Z)-hex-3-en-1-yl 2-hydroxybenzoate; 2-ethyl-4-hydroxy-5-methylfuran-3(2H)-one; (E)-4-(2,6,6-trimethylcyclohex-1-en-1-yl)but-3-en-2-one; (E)-3-methyl-4-(2,6,6-trimethylcyclohex-2-en-1-yl)but-3-en-2-one; 1-(2,3,8,8-tetramethyl-1,2,3,4,5,6,7,8-octahydronaphthalen-2-yl)ethanone; 4-formyl-2-methoxyphenyl isobutyrate; (E)-2-methoxy-4-(prop-1-en-1-yl)phenol; 6-isopropylquinoline; (1-methyl-2-(1,2,2-trimethylbicyclo[3.1.0]hexan-3-yl)methyl)cyclopropyl) methanol; 5-(sec-butyl)-2-(2,4-dimethylcyclohex-3-en-1-yl)-5-methyl-1,3-dioxane; Benzoic acid, 2-hydroxy-, (3Z)-1-methyl-3-hexen-1-yl ester; 6,8-Nonadien-3-one, 2,4,4,7-tetramethyl-, oxime; 8-isopropyl-1-oxaspiro[4.5]decan-2-one; 3-(4-(tert-butyl)phenyl)-2-methylpropanal; 3,7-dimethylocta-1,6-dien-3-yl cinnamate; 2,4-dimethyl-4,4a,5,9b-tetrahydroindeno[1,2-d][1,3]dioxine; 3-hydroxy-2-methyl-4H-pyran-4-one; 3-methyl-5-phenylpentanol; methyl 2-aminobenzoate; 8-methyl-1-oxaspiro[4.5]decan-2-one; Naphth[2,3-b]oxirene, 1a,2,3,4,5,6,7,7a-octahydro-1a,3,3,4,6,6-hexamethyl-, (1aR,4S,7aS)-rel-; (Z)-3-methylcyclopentadec-5-enone; 1,4-dioxacyclohexadecane-5,16-dione; Cyclopentadecanone; 1-(4-(tert-butyl)-2,6-dimethyl-3,5-dinitrophenyl)ethanone; 1,7-dioxacycloheptadecan-8-one; benzene, 1-(1,1-dimethylethyl)-3,5-dimethyl-2,4,6-trinitro-; 2-methylundecanoic acid; 2-(2-(4-methylcyclohex-3-en-1-yl)propyl)cyclopentanone; 2-ethoxynaphthalene; (E)-13-methyloxacyclopentadec-10-en-2-one; (2E,6Z)-nona-2,6-dienal; (2E,6Z)-nona-2,6-dien-1-ol; 4,4a-dimethyl-6-(prop-1-en-2-yl)-4,4a,5,6,7,8-hexahydronaphthalen-2(3H)-one; 5-butyldihydrofuran-2(3H)-one; 1-naphthalen-2-ylethanone; 3-methoxy-5-methylphenol; p-tolyl 2-phenylacetate; 2-ethyl-N-methyl-N-(m-tolyl)butanamide; 5-heptyldihydrofuran-2(3H)-one; 2-cyclohexylidene-2-phenylacetonitrile; Benzeneacetonitrile, alpha-cyclohexylidene-2-methyl-; 2-cyclohexylhepta-1,6-dien-3-one; 2-phenylacetic acid; phenethyl acetate; 2-phenylethanol; phenyl-(E)-3-phenylprop-2-enoate; phenethyl 2-hydroxybenzoate; (E)-3,3-dimethyl-5-(2,2,3-trimethyl-3-cyclopenten-1-yl)-4-penten-2-ol; 2-ethoxy-4-(isopropoxymethyl)phenol; 5-pentyldihydrofuran-2(3H)-one; 6-(sec-butyl)quinoline; (E)-2-ethyl-4-(2,2,3-trimethylcyclopent-3-en-1-yl)but-2-en-1-ol; 4-(4-hydroxyphenyl)butan-2-one; 2-methyl-5-phenylpentan-1-ol; 4-methylene-2-phenyltetrahydro-2H-pyran; (3S,5R,8S)-5-Isopropenyl-3,8-dimethyl-3,4,5,6,7,8-hexahydro-1(2H)-azulenone; (2-butenol-2-methyl-4-(2,3-trimethyl-3-cyclopenten-1-yl); 2,5-dimethyl-4-methoxy-3(2H)furanone; 2-(1-(3,3-dimethylcyclohexyl)ethoxy)-2-methylpropyl cyclopropanecarboxylate; 3-(4-isobutylphenyl)-2-methylpropanal; ethyl-3-methylé-3-phenyloxirane-2-carboxylate; (E)-2-((3,5-dimethylhex-3-en-2-yl)oxy)-2-methylpropyl cyclopropanecarboxylate; oxacyclohexadecan-2-one; 1-(2,2,6-trimethylcyclohexyl)hexan-3-ol; 4-oxo-4-[(2S,3S)-1,1,2,6-tetramethyl-3-(propan-2-yl)-2,3-dihydro-1H-inden-5-yl]butanoic acid; (E)-tridec-2-enenitrile; 1-((2E,5Z,9Z)-2,7,8-trimethylcyclododeca-2,5,9-trien-1-yl)ethanone; 3-(benzo[d][1,3]dioxol-5-yl)-2-methylpropanal; 2-ethoxy-4-methylphenol; 4-hydroxy-3-methoxybenzaldehyde; (2E,6Z)-nona-2,6-dienenitrile; 1-((1S,8aS)-1,4,4,6-tetramethyl-2,3,3a,4,5,8-hexahydro-1H-5,8a-methanoazulen-7-yl) ethanone; 2,4-diethoxy-5-methylpyrimidine; 2-methoxynaphthalene; Patchouli oil; (E)-9-hydroxy-5,9-dimethyldec-4-enal; 3-(4-isobutyl-2-methylphenyl)propanal; 2-(2-(4-methyl cyclohex-3-en-1-yl)allyl)cyclopentanone; 1-((1S,4R,8R)-1,8-dimethyl-2-oxabicyclo[2.2.2]octan-5-yl)ethanol; 41S,4R,7S)-3,6,7-trimethyl-2-oxabicyclo[2.2.2]octan-5-yl)methanol; 9-hydroxy-5,9-dimethyldecanal; (S)-2-((2S,4aR)-1,1,5,5-tetramethyl-2,3,4,5,6,7-hexahydro-1H-2,4a-methanonaphthalen-8-yl)butan-1-ol; (R)-2-((2S,4aS,8aS)-1,1,5,5-tetramethyl-2,3,4,5,6,8a-hexahydro-1H-2,4a-methanonaphthalen-8-yl)butan-1-ol; (3aR,5aS,8S,9aR,9bS)-2,2,3a,5,5,9,9-heptamethyloctahydro-3aH-5a,8-methanonaphtho[1,2-d][1,3]dioxole; (1-methyl-2-(5-methylhex-4-en-2-yl)cyclopropyl)methanol; (E)-7-(4-methylpent-1-en-1-yl)-2H-benzo[b][1,4]dioxepin-3(4H)-one.

Perfume ingredients conforming to this definition are deemed to be coherent relative to each other according to how that term is understood in the present invention.

A third grouping of perfume ingredients, referred to hereafter as INGREDIENT GROUP 3, is characterised in that they belong to INGREDIENT GROUP 1 and are further characterised in that they are crystalline at room temperature (20° C.).

When 10 microliters of a solution of 0.24% by weight of an INGREDIENT GROUP 3 ingredient in a solvent mixture comprising 76.4% ethanol, 10% tri-ethyl citrate and 3.6% water is placed on an etched glass substrate and left for 4 hours at a temperature of 32° C.+/−2° C. before being placed at a temperature of 32° C.+/−2° C., under aforementioned flow and room convection conditions, this ingredient will be detectable 2 metres downstream of the substrate within a detection time of 5 to 60 seconds on average and with an average intensity larger than 1 on a scale of 10, as defined above.

This third group of ingredients comprises: (E)-2-methoxy-4-(prop-1-en-1-yl)phenyl acetate; 4-formyl-2-methoxyphenyl acetate; 1-42-(tert-butyl)cyclohexyl)oxy) butan-2-ol; 3,8,8,11a-tetramethyldodecahydro-1H-3,5a-epoxynaphtho[2,1-c]oxepine1,3,4,5,6,7-hexahydro-.beta.,1,1,5,5-pentamethyl-2H-2,4a-methanonaphthalene-8-ethanol; (4aR,5R,7 aS,9R)-octahydro-2,2,5,8,8,9a-hexamethyl-4h-4a,9-methano azuleno (5,6-d)-1,3-dioxole; 3a,6,6,9a-tetramethyldodecahydronaphtho[2,1-b]furan; ((1S,8aR)-1,4,4-trimethyl-2,3,3a,4,5,8-hexahydro-1H-5,8a-methanoazulen-6-yl)methanol; 7-isopentyl-2H-benzo[b][1,4]dioxepin-3(4H)-one; 7-methyl-2H-benzo[b][1,4]dioxepin-3(4H)-one; 3-hydroxy-4,5-dimethylfuran-2(5H)-one; 4-(1,3-benzodioxol-5-yl)butan-2-one; (1S,6R,8aR)-1,4,4,6-tetramethyloctahydro-1H-5,8a-methanoazulen-6-ol; (1S,6R,8aR)-1,4,4,6-tetramethyloctahydro-1H-5,8a-methanoazulen-6-yl acetate; methyl 2,4-dihydroxy-3-methylbenzoate; 3-phenylprop-2-enoic acid; 2-hydroxy-3-methylcyclopent-2-enone; 2H-chromen-2-one; p-tolyl 2-phenylacetate; 3-phenylprop-2-enyl 3-phenylprop-2-enoate; 2-ethyl-3-hydroxy-4H-pyran-4-one; 3-ethoxy-4-hydroxybenzaldehyde; methyl 2,4-dihydroxy-3,6-dimethylbenzoate; 1-(3,5,5,6,8,8-hexamethyl-5,6,7,8-tetrahydronaphthalen-2-yl)ethanone; benzo[d][1,3]dioxole-5-carbaldehyde; 2-ethyl-4-hydroxy-5-methylfuran-3(2H)-one; 1H-indole; 6,8-Nonadien-3-one, 2,4,4,7-tetramethyl-, oxime; 3-hydroxy-2-methyl-4H-pyran-4-one; hexyl (E)-3-phenylprop-2-enoate; Naphth[2,3-b]oxirene, 1a,2,3,4,5,6,7,7a-octahydro-1a,3,3,4,6,6-hexamethyl-, (1aR,4S,7aS)-rel-; (Z)-3-methylcyclopentadec-5-enone; Cyclopentadecanone; 1-(4-(tert-butyl)-2,6-dimethyl-3,5-dinitrophenyl)ethanone; 1,7-dioxacycloheptadecan-8-one; 2-methylundecanoic acid; 2-ethoxynaphthalene; 4,4a-dimethyl-6-(prop-1-en-2-yl)-4,4a,5,6,7,8- hexahydronaphthalen-2(3H)-one; 1-naphthalen-2-ylethanone; 3-methoxy-5-methylphenol; Benzeneacetonitrile, alpha-cyclohexylidene-2-methyl-; 2-cyclohexylidene-2-phenylacetonitrile; 2-phenylacetic acid; phenyl-(E)-3-phenylprop-2-enoate; phenethyl 2-hydroxybenzoate; 2-methyl-5-phenylpentan-1-ol; 2,2,2-trichloro-1-phenylethyl acetate; 2,5-dimethyl-4-methoxy-3(2H)furanone; 3-methyl-1H-indole; oxacyclohexadecan-2-one; 4-hydroxy-3-methoxybenzaldehyde; 2-methoxynaphthalene.

Preferred INGREDIENT GROUP 3 are 3,8,8,11a-tetramethyldodecahydro-1H-3,5a-epoxynaphtho[2,1-c]oxepine; 1,3,4,5,6,7-hexahydro-.beta., 1,1,5,5-pentamethyl-2H-2,4a-methanonaphthalene-8-ethanol; (4aR,5R,7aS,9R)-octahydro-2,2,5,8,8,9a-hexamethyl-4h-4a,9-methanoazuleno(5,6-d)-1,3-dioxole; 3a,6,6,9a-tetramethyldodecahydronaphtho[2,1-b]furan; 7-isopentyl-2H-benzo[b][1,4]dioxepin-3(4H)-one; 7-methyl-2H-benzo[b][1,4]dioxepin-3(4H)-one; 2H-chromen-2-one; 2-ethyl-3-hydroxy-4H-pyran-4-one; 3-ethoxy-4-hydroxybenzaldehyde; methyl 2,4-dihydroxy-3,6-dimethylbenzoate; 1-(3,5,5,6,8,8-hexamethyl-5,6,7,8-tetrahydronaphthalen-2-yl)ethanone; benzo[d][1,3]dioxole-5-carbaldehyde; 2-ethyl-4-hydroxy-5-methylfuran-3(2H)-one; 1H-indole; 3-hydroxy-2-methyl-4H-pyran-4-one; naphth[2,3-b]oxirene, 1a,2,3,4,5,6,7,7a-octahydro-1a,3,3,4,6,6-hexamethyl-, (1aR,4S,7aS)-rel-; (Z)-3-methylcyclopentadec-5-enone; cyclopentadecanone; 1-(4-(tert-butyl)-2,6-dimethyl-3,5-dinitrophenyl)ethanone; 2-methylundecanoic acid; 2-ethoxynaphthalene; 1-naphthalen-2-ylethanone; benzeneacetonitrile, alpha-cyclohexylidene-2-methyl-; 2-methyl-5-phenylpentan-1-ol; 2,2,2-trichloro-1-phenylethyl acetate; oxacyclohexadecan-2-one; 4-hydroxy-3-methoxybenzaldehyde; 2-methoxynaphthalene.

Perfume ingredients conforming to this definition are deemed to be coherent relative to each other according to how that term is understood in the present invention.

A fourth grouping of perfume ingredients, referred to hereafter as INGREDIENT GROUP 4, are characterised in that they belong to INGREDIENT GROUP 2, but are characterized by a superior performance in terms of intensity at distance, and are not crystalline in their pure state at room temperature (20° C.).

When 10 microliters of a solution of 0.24% by weight of an INGREDIENT GROUP 4 ingredient in a solvent mixture comprising 76.4% ethanol, 10% tri-ethyl citrate and 3.6% water are placed on a substrate and left for 4 hours at a temperature of 32° C.+/−2° C. before being placed at a temperature of 32° C.+/−2° C., under aforementioned flow and room convection conditions, this ingredient will be detectable 2 metres downstream of the substrate within a detection time of 5 to 60 seconds and with an average intensity larger than 2.4 on a scale of 10, as defined above.

This fourth group of ingredients comprises:
(Z)-oxacycloheptadec-10-en-2-one; 4-methoxybenzaldehyde; 3-(4-(tert-butyl)phenyl)propanal; 2-(2-mercaptopropan-2-yl)-5-methylcyclohexanone; (Z)-3-methylcyclotetradec-5-enone; 4-(4-hydroxy-4-methylpentyl)cyclohex-3-enecarbaldehyde; (E)-1-(2,6,6-trimethylcyclohexa-1,3-dien-1-yl)but-2-en-1-one; (E)-1-(2,6,6-trimethyl cyclo hex-1-en-1-yl)but-2-en-1-one; (E)-1-(2,6,6-trimethylcyclohex-3-en-1-yl)but-2-en-1-one; 6-pentyltetrahydro-2H-pyran-2-one; 2-(2-(3,3,5-trimethylcyclohexyl)acetyl)cyclopentanone; 6-heptyltetrahydro-2H-pyran-2-one; 8-ethyl-1-oxaspiro[4.5]decan-2-one; 6-pentyltetrahydro-2H-pyran-2-one; 4-allyl-2-methoxyphenol; 3-(3-isopropylphenyl)butanal; 1-(3,3-dimethylcyclohex-1-en-1-yl)pent-4-en-1-one; 2-isobutylquinoline; (E)-2-methoxy-4-(prop-1-en-1-yl)phenol; 6-isopropylquinoline; (1-methyl-2-((1,2,2-trimethylbicyclo[3.1.0]hexan-3-yl)methyl)cyclopropyl)methanol; 3-(4-(tert-butyl)phenyl)-2-methylpropanal; 3-methyl-5-phenylpentanol; 8-methyl-1-oxaspiro[4.5]decan-2-one; methyl 2-aminobenzoate; 2-(2-(4-methylcyclohex-3-en-1-yl)propyl)cyclopentanone; (2E,6Z)-nona-2,6-dienal; 5-heptyldihydrofuran-2(3H)-one; 2-cyclohexylhepta-1,6-di en-3-one; (E)-2-ethyl-4-(2,2,3-trimethylcyclopent-3-en-1-yl)but-2-en-1-ol; 4-methyl ene-2-phenyltetrahydro-2H-pyran; (Z)-hex-3-en-1-yl 2-hydroxybenzoate; 2,4-diethoxy-5-methylpyrimidine; (2E,6Z)-nona-2,6-dienenitrile; Patchouli oil; (E)-9-hydroxy-5,9-dimethyldec-4-enal; 3-(4-isobutyl-2-methylphenyl)propanal; 2-(2-(4-methyl cyclohex-3-en-1-yl)allyl)cyclopentanone.

Preferred INGREDIENT GROUP 4 are (Z)-oxacycloheptadec-10-en-2-one; 4-methoxybenzaldehyde; 3-(4-(tert-butyl)phenyl)propanal; 2-(2-mercaptopropan-2-yl)-5-methylcyclohexanone; (Z)-3-methylcyclotetradec-5-enone; 4-(4-hydroxy-4-methylpentyl)cyclohex-3-enecarbaldehyde; (E)-1-(2,6,6-trimethylcyclohexa-1,3-dien-1-yl)but-2-en-1-one; (E)-1-(2,6,6-trimethylcyclohex-3-en-1-yl)but-2-en-1-one; 8-ethyl-1-oxaspiro[4.5]decan-2-one; 4-allyl-2-methoxyphenol; (E)-2-methoxy-4-(prop-1-en-1-yl)phenol; (1-methyl-2-((1,2,2-trimethylbicyclo[3.1.0]hexan-3-yl)methyl)cyclopropyl)methanol; 3-(4-(tert-butyl)phenyl)-2-methylpropanal; 3-methyl-5-phenylpentanol; 8-methyl-1-oxaspiro[4.5]decan-2-one; methyl 2-aminobenzoate; 2-(2-(4-methyl cyclohex-3-en-1-yl)propyl)cyclopentanone; (2E,6Z)-nona-2,6-dienal; 5-heptyldihydrofuran-2(3H)-one; 2-cyclohexylhepta-1,6-dien-3-one; (E)-2-ethyl-4-(2,2,3-trimethyl cyclopent-3-en-1-yl)but-2-en-1-ol; 4-methyl ene-2-phenyltetrahydro-2H-pyran; (Z)-hex-3-en-1-yl 2-hydroxybenzoate; (E)-9-hydroxy-5,9-dimethyldec-4-enal; 3-(4-isobutyl-2-methylphenyl)propanal.

Perfume ingredients conforming to this definition are deemed to be coherent relative to each other according to how that term is understood in the present invention.

A fifth grouping of perfume ingredients, referred to hereafter as INGREDIENT GROUP 5, are characterised in that they belong to INGREDIENT GROUP 2 and are crystalline at room temperature (20° C.).

When 10 microliters of a solution of 0.24% by weight of an INGREDIENT GROUP 5 ingredient in a solvent mixture comprising 76.4% ethanol, 10% tri-ethyl citrate and 3.6% water are placed on a substrate and left for 4 hours at a temperature of 32° C.+/−2° C. before being placed at a temperature of 32° C.+/−2° C., under aforementioned flow and room convection conditions, this ingredient will be detectable 2 metres downstream of the substrate within a detection time of 5 to 60 seconds and with an average intensity larger than on a scale of 10.

This fifth group ingredients comprise: 3,8,8,11a-tetramethyldodecahydro-1H-3,5a-epoxynaphtho[2,1-c]oxepine; (2,4a,5,8a-tetramethyl-1,2,3,4,7,8-hexahydronaphthalen-1-yl) formate; (4aR,5R,7 aS,9R)-octahydro-2,2,5,8,8,9a-hexamethyl-4h-4a,9-methano azuleno (5,6-d)-1,3-dioxole; 3a,6,6,9a-tetramethyldodecahydronaphtho[2,1-b]furan; 7-isopentyl-2H-benzo[b][1,4]dioxepin-3 (4H)-one; 7-methyl-2H-benzo[b][1,4]dioxepin-3 (4H)-one; 3-hydroxy-4,5-dimethylfuran-2 (5H)-one; 3a,6,6,9a-tetramethyldodecahydronaphtho[2,1-b]furan; methyl 2,4-dihydroxy-3-methylbenzoate; 2H-chromen-2-one; 2-ethyl-3-hydroxy-4H-pyran-4-one; 3-ethoxy-4-hydroxybenzaldehyde; methyl 2,4-dihydroxy-3,6-dimethylbenzoate; 1-(4-(tert-butyl)-2,6-dimethyl-3,5-dinitrophenyl)ethanone; 2-methylundecanoic acid; 1-naphthalen-2-ylethanone; 2-phenylacetic acid; 2-methyl-5-phenylpentan-1-ol; and 3-methyl-1H-indole; 4-hydroxy-3-methoxybenzaldehyde.

Perfume ingredients conforming to this definition are deemed to be coherent relative to each other according to how that term is understood in the present invention.

Perfume compositions comprising mixtures of the INGREDIENT GROUP 2, 3, 4 and 5 will exhibit a coherent, fast developing and prolonged olfactory impact at a distance from the compositions' source, when submitted to convection flows, and to a skilled evaluator the composition will have a readily recognisable olfactory profile. In this way, perfumers will be able to design new perfumery products that will have, with use, an instantly memorable signature recognisable by consumers that will lead to greater consumer acceptance. Such coherent perfume compositions are to be contrasted with perfume compositions that have an incoherent olfactory impact, which exhibit sequentially different fragrance impressions, e.g. floral, powdery etc. before the full perfume impact evolves over time.

Accordingly, in another aspect of the present invention there is provided a perfume composition comprising two or more perfume ingredients selected from those ingredients belonging to GROUP 2, 3, 4 and 5 according to the following rules:

1) The sum of the concentrations in weight percentage (wt %) of ingredients selected from GROUP 2 is at least 10 wt %, more particularly between 10 wt % and 100 wt %, more particularly between 25 wt % and 90 wt %, and still more particularly between 40 wt % and 70 wt % by weight,
AND
2) The sum of the concentrations of ingredients of GROUP 3, 4 and 5, each ingredient counted only once in the sum, is at least 5 wt %, more particularly between 5 and 60 wt %, more particularly between 7.5 wt % and 50 wt % and still more particularly between 10 wt % and 40 wt %.
AND/OR
3) The sum of the concentrations of ingredients selected from GROUP 5 is at least 0.1 wt %, more particularly between 0.1 wt % and 30 wt %, more particularly between 0.5 wt % and 20 wt % and still more particularly between 1 wt % and 15 wt %.

Perfume compositions according to the present invention need not be limited to a mixture of those perfume ingredients mentioned above. Other ingredients commonly used in perfumery may be employed to form the balance of perfume ingredients. Any of those ingredients described in "Perfume and Flavour Chemicals", S. Arctander, Allured Publishing Corporation, 1994, IL, USA, which is incorporated herein by reference.

Perfume compositions of the present invention and consumer products containing same may 30 also contain commonly employed adjuvants. The term "adjuvants" refers to ingredients that may affect the performance of a composition, other than its hedonic performance. For example, an adjuvant may be an ingredient that acts as an aid to processing a perfume composition or consumer product containing said composition, or it may improve handling or storage of a perfume composition or consumer product. It might also be an ingredient that provides additional benefits such as imparting colour or texture. It might also be an ingredient that imparts light resistance or chemical stability to one or more ingredients contained in a perfume composition or consumer product. A detailed description of the nature and type of adjuvants commonly used in perfume compositions or consumer products cannot be exhaustive, but it has to be mentioned that said ingredients are well known to a person skilled in the art. Examples of adjuvants include solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

One or more of the perfume ingredients or adjuvants employed in perfume compositions or consumer products may be formulated in a delivery vehicle to provide a desired effect. Delivery vehicles may include capsule technologies. Alternatively, the delivery vehicle may be in the form of a solid support, e.g. a polymeric support material onto which one or more perfume ingredients may be chemically or physically bound. Still further, one or more perfume ingredients may be dissolved or dispersed in a matrix material, which serves to control the rate at which said ingredient or ingredients emanates. In yet an alternative embodiment, one or more ingredients may be supported on a porous substrate, such as a cyclodextrin or a zeolite or other inorganic material. In a still further embodiment, one or more ingredients may be provided in the form of a pro-perfume, which will react in a suitable environment to release the perfume ingredient in a controlled manner.

Perfume compositions of the present invention may be employed in all manner of personal and home care consumer products known in the art. A non-limiting list of applications include a textile treatment product, an ironing aid, a cleaning cloth, a laundry detergent, a cleaning product, in particular, for hard and/or soft surfaces, a household cleaner, a care product, a wash care product, a laundry care product, a room fragrancer, and air freshener, a conditioner, a colorant, a fabric conditioner, a conditioning substrate, a pharmaceutical, a crop protection product, a polish, a food, a cosmetic product, a fertilizer, a building material, an adhesive, a bleach, a decalcifier, an auto care product, floor care product, cooker care product, leather care product or furniture care product, a scourer, a disinfectant, a fragrancer, a mould remover, fine fragrance, body lotion, skin care preparations, candles, air fresheners, plug ins and toilet soaps.

Particular examples of cleaning products include the toilet cleaners or lavatory cleaners, these products being supplied in the form of powders, blocks, tablets or liquids, or gels, pipe-cleaning products or drain cleaners, universal or all-purpose or general-purpose cleaners, such as those used universally for all hard surfaces in the household and in commerce that can be wiped down wet or damp, sanitary cleaners, oven cleaners or grill cleaners which may be presented in the form of gels or foam sprays, metal polishes, including those supplied as polishing cloths, dipping baths, pastes, and liquids; glass cleaners and window cleaners; all special-purpose cleaning products, for example those for glass-ceramic hobs; carpet cleaners and stain removers.

Particular examples of auto care products include paint preservers, paint polishes, paint cleaners, wash preservers, shampoos for auto washing, auto-wash and wax products, polishes for trim metals, protective films for trim metals, plastics cleaners, tar removers, screen cleaners, engine cleaners and the like.

Particular examples of cosmetic products include cosmetic skincare products, e.g. bath products, skin washing and cleansing products, skincare products, eye makeup, lip care products, nail care products, intimate care products, foot care products; cosmetic products with specific effects, such as sunscreens, tanning products, de-pigmenting products, deodorants, antiperspirants, hair removers, shaving products; cosmetic dental-care products, such as dental and oral care products, toothcare products, cleaners for dental prostheses, adhesives for dental prostheses; cosmetic hair care products, e.g. hair shampoos, hair care products, hair setting products, hair-shaping products, and hair colouring products. Particular examples of textile treatment products include detergents or fabric conditioners. Particular examples of air fresheners and room fragrancers include fragrancers for spaces such as autos, cupboards, dishwashers, refrigerators or shoes, and vacuum cleaners.

In a particular embodiment of the present invention the perfume composition is employed in a fine fragrance composition. More particularly, in a fine fragrance application said perfume composition may be diluted in a hydroalcoholic base, comprising 0 to 50 wt %, more particularly 0.5 to 30 wt %, still more particularly 1 to 25 wt % water. Alternatively, in a fine fragrance application the perfume composition may be presented in the form of a microemulsion, wherein said perfume composition is present in an amount of 1 to 50 wt %, more particularly 3 to 40 wt %, and still more particularly between 5 and 30 wt % based on the total weight of the composition.

There now follows a series of examples that serve to illustrate the invention.

EXAMPLE 1

0.24% by weight of the following perfumery ingredients are dissolved in 99.76% of a mixture comprising 76.4% ethanol, 10% tri-ethyl citrate and 3.6% water; and 10 microliters of this solution are placed on a etched glass plates having a etched surface of 0.4×1.8 cm$^2$ and a total surface of 0.5×2 cm$^2$ and let to evaporate for 4 hours at a temperature of 32° C.+/−2° C. Each plate is then inserted in the device as described above and submitted to aforementioned flow and room convection conditions, whereas the optimal measurement conditions for said room were obtained by setting the air flow at 20 ml/min. The odour intensity is then measured at the outlet of the channel at least 5 trained panelists and reported in Table 1. All ingredients are detected within 60 seconds in average. The scores obtained by panelists deemed anosmic to a particular ingredient are removed.

Ingredients having an average intensity higher than 7 were given a Score Class A; ingredients having an average intensity ranging from 6 to 7 were given a Score Class B; ingredients having an average intensity ranging from 5 to 6 were given a Score Class C; ingredients having an average intensity ranging from 3 to 5 were given a Score Class D and ingredients having an average intensity ranging from 1 to 3 were given a Score Class E and the ingredients having an average intensity lower than 1 were given a Score Class F.

TABLE 1

| PERFUMERY INGREDIENT | AVERAGE INTENSITY |
| --- | --- |
| 3-hydroxy-4,5-dimethylfuran-2(5H)-one | A |
| (2,4a,5,8a-tetramethyl-1,2,3,4,7,8-hexahydronaphthalen-1-yl) formate | A |
| 7-isopentyl-2H-benzo[b][1,4]dioxepin-3(4H)-one | A |
| 2-methylundecanoic acid | A |
| 8-ethyl-1-oxaspiro[4.5]decan-2-one | A |
| (1-methyl-2-((1,2,2-trimethylbicyclo[3.1.0]hexan-3-yl)methyl)cyclopropyl)methanol | A |
| 1-(spiro[4.5]dec-7-en-7-yl)pent-4-en-1-one | A |
| (2E,6Z)-nona-2,6-dienenitrile | A |
| 4-(4-hydroxyphenyl)butan-2-one | A |

TABLE 1-continued

| PERFUMERY INGREDIENT | AVERAGE INTENSITY |
| --- | --- |
| 3-ethoxy-4-hydroxybenzaldehyde | A |
| 2-cyclohexylhepta-1,6-dien-3-one | A |
| 4-methylene-2-phenyltetrahydro-2H-pyran | A |
| (3S,5R,8S)-5-Isopropenyl-3,8-dimethyl-3,4,5,6,7,8-hexahydro-1(2H)-azulenone | A |
| Patchouli oil | A |
| 2-(2-mercaptopropan-2-yl)-5-methylcyclohexanone | A |
| 2-ethyl-4-hydroxy-5-methylfuran-3(2H)-one | A |
| 4-allyl-2-methoxyphenol | B |
| 1-(3,3-dimethylcyclohex-1-en-1-yl)pent-4-en-1-one | B |
| 5-heptyldihydrofuran-2(3H)-one | B |
| 6-pentyltetrahydro-2H-pyran-2-one | B |
| 2-methoxynaphthalene | B |
| methyl 2,4-dihydroxy-3,6-dimethylbenzoate | B |
| 2H-chromen-2-one | B |
| 7-methyl-2H-benzo[b][1,4]dioxepin-3(4H)-one | B |
| (E)-2-methoxy-4-(prop-1-en-1-yl)phenol | B |
| (2E,6Z)-nona-2,6-dienal | B |
| 3-methyl-5-phenylpentanol | B |
| 4-(4-hydroxy-4-methylpentyl)cyclohex-3-enecarbaldehyde | B |
| 4-hydroxy-3-methoxybenzaldehyde | C |
| 3a,6,6,9a-tetramethyldodecahydronaphtho[2,1-b]furan | C |
| 5-octyldihydrofuran-2(3H)-one | C |
| 1-(4-(tert-butyl)-2,6-dimethyl-3,5-dinitrophenyl)ethanone | C |
| 1-naphthalen-2-ylethanone | C |
| methyl 2-(3-oxo-2-pentylcyclopentyl)acetate | C |
| 2,4-diethoxy-5-methylpyrimidine | C |
| (E)-1-(2,6,6-trimethylcyclohexa-1,3-dien-1-yl)but-2-en-1-one | C |
| 3a,6,6,9a-tetramethyldodecahydronaphtho[2,1-b]furan | C |
| 8-methyl-1-oxaspiro[4.5]decan-2-one | D |
| (Z)-oxacycloheptadec-10-en-2-one | D |
| (E)-2-ethyl-4-(2,2,3-trimethylcyclopent-3-en-1-yl)but-2-en-1-ol | D |
| 4-methoxybenzaldehyde | D |
| (E)-1-(2,6,6-trimethylcyclohex-3-en-1-yl)but-2-en-1-one | D |
| 6-isopropylquinoline | D |
| 2-(2-(4-methylcyclohex-3-en-1-yl)propyl)cyclopentanone | D |
| 3-(3-isopropylphenyl)butanal | D |
| (Z)-3-methylcyclopentadec-5-enone | D |
| 3,8,8,11a-tetramethyldodecahydro-1H-3,5a-epoxynaphtho[2,1-c]oxepine | D |
| 3-(4-(tert-butyl)phenyl)-2-methylpropanal | D |
| methyl 2-aminobenzoate | D |
| (E)-1-(2,6,6-trimethylcyclohex-1-en-1-yl)but-2-en-1-one | D |
| (E)-methyl 2-((7-hydroxy-3,7-dimethyloctylidene)amino)benzoate | D |
| 2-isobutylquinoline | D |
| 2-(2-(3,3,5-trimethylcyclohexyl)acetyl)cyclopentanone | E |
| 2-ethyl-3-hydroxy-4H-pyran-4-one | E |
| p-tolyl octanoate | E |
| 3-(4-(tert-butyl)phenyl)propanal | E |
| Benzeneacetonitrile, alpha-cyclohexylidene-2-methyl- | E |
| (Z)-3-methylcyclotetradec-5-enone | E |
| 2-nonenal | E |
| (Z)-(Z)-hex-3-en-1-yl hex-3-enoate | E |
| 8-isopropyl-1-oxaspiro[4.5]decan-2-one | E |
| (E)-tridec-2-enenitrile | E |
| (E)-2-methoxy-4-(prop-1-en-1-yl)phenyl acetate | E |

TABLE 1-continued

| PERFUMERY INGREDIENT | AVERAGE INTENSITY |
|---|---|
| 1-(pyrazin-2-yl)ethanone | E |
| 1,4-dioxacycloheptadecane-5,17-dione | E |
| (E)-4-((3aS,7aS)-hexahydro-1H-4,7-methanoinden-5(6H)-ylidene)butanal | E |
| benzo[d][1,3]dioxole-5-carbaldehyde | E |
| 6,8-Nonadien-3-one, 2,4,4,7-tetramethyl-, oxime | E |
| 2-methylundecanal | E |
| 6-propyltetrahydro-2H-pyran-2-one | E |
| 2-(sec-butyl)-1-vinylcyclohexyl acetate | E |
| 1-((2E,5Z,9Z)-2,7,8-trimethylcyclododeca-2,5,9-trien-1-yl)ethanone | E |
| (E)-4-(2,6,6-trimethylcyclohex-1-en-1-yl)but-3-en-2-one | E |
| 3,7-dimethylocta-1,6-dien-3-yl cinnamate | E |
| benzyl 2-hydroxybenzoate | E |
| 4-(1,3-benzodioxol-5-yl)butan-2-one | E |
| 5-(sec-butyl)-2-(2,4-dimethylcyclohex-3-en-1-yl)-5-methyl-1,3-dioxane | E |
| 3-hydroxy-2-methyl-4H-pyran-4-one | E |
| 3-(benzo[d][1,3]dioxol-5-yl)-2-methylpropanal | E |
| 1H-indole | E |
| 2,4-dimethyl-4,4a,5,9b-tetrahydroindeno[1,2-d][1,3]dioxine | E |
| 3-methylcyclopentadecanone | E |
| 3-((1R,2S,4R,6R)-5,5,6-trimethylbicyclo[2.2.1]heptan-2-yl)cyclohexanol | E |
| 4-[(6,6-dimethyl-5-bicyclo[2.2.1]heptanyl)methyl]-2-methylcyclohexan-1-one | E |
| 5-pentyldihydrofuran-2(3H)-one | E |
| methyl 2-(3-oxo-2-pentylcyclopentyl)acetate | E |
| (E)-dec-4-enal | E |
| (Z)-cycloheptadec-9-enone | E |
| 1-(3,5,5,6,8,8-hexamethyl-5,6,7,8-tetrahydronaphthalen-2-yl)ethanone | E |
| oxacyclohexadecan-2-one | E |
| (1R,6S,8aS)-6-methoxy-1,4,4,6-tetramethyloctahydro-1H-5,8a-methanoazulene | E |
| (E)-oxacyclohexadec-12-en-2-one | E |
| (E)-3-methyl-4-(2,6,6-trimethylcyclohex-2-en-1-yl)but-3-en-2-one | E |
| 4-formyl-2-methoxyphenyl isobutyrate | E |
| 2-ethoxynaphthalene | E |
| 2-(1-(3,3-dimethylcyclohexyl)ethoxy)-2-methylpropyl cyclopropanecarboxylate | E |
| octahydro-2H-chromen-2-one | E |
| (ethoxymethoxy)cyclododecane | E |
| 2,4-dimethyl-2-(5,5,8,8-tetramethyl-5,6,7,8-tetrahydronaphthalen-2-yl)-1,3-dioxolane | E |
| 4,6,6,7,8,8-hexamethyl-1,3,4,6,7,8-hexahydrocyclopenta[g]isochromene | F |
| 1,4-dioxacyclohexadecane-5,16-dione | F |
| 1-(2,2,6-trimethylcyclohexyl)hexan-3-ol | F |
| (E)-3-phenylprop-2-en-1-ol | F |
| (E)-3,3-dimethyl-5-(2,2,3-trimethyl-3-cyclopenten-1-yl)-4-penten-2-ol | F |
| 6-propyltetrahydro-2H-pyran-2-one | F |
| 1-(1,2,8,8-tetramethyl-1,2,3,4,5,6,7,8-octahydronaphthalen-2-yl)ethanone | F |
| (4-methoxyphenyl)methanol | F |
| (E)-3-methyl-5-(2,2,3-trimethylcyclopent-3-en-1-yl)pent-4-en-2-ol | F |
| 1-((2-(tert-butyl)cyclohexyl)oxy)butan-2-ol | F |
| 1-(2,3,8,8-tetramethyl-1,2,3,4,5,6,7,8-octahydronaphthalen-2-yl)ethanone | F |
| 3-(4-isobutylphenyl)-2-methylpropanal | F |
| allyl 2-phenoxyacetate | F |

EXAMPLE 2

The formulations of a series of perfumes are reported in Table 2 as illustrative but not limitative examples. The sums of the concentrations of the ingredients in each GROUP are also reported in Table 2. The intensity at distance was measured according to the following procedures: 10 microliters of a solution of 10% perfume in solvent comprising 96% ethanol and 4% water (hydro-alcoholic solution) are placed on a etched glass plates having a etched surface of 0.4×1.8 cm$^2$ and a total surface of 0.5×2 cm$^2$ and let to evaporate for 4 hours at a temperature of 32° C.+/−2° C. Each plate is then inserted in the device as described above and submitted to aforementioned flow and room convection conditions, whereas the optimal measurement conditions for said room were obtained by setting the air flow at 20 ml/min. The odour intensity is then measured at the outlet of the channel (i.e. 2 m away from the source) by at least 5 trained panelists and reported in Table 2. Perfumes having an average intensity higher than 7 were given a score "+++"; perfumes having an average intensity ranging from 4 to 7 were given a score "++"; perfumes having an average intensity ranging from 1 to 4 were given a score "+" and perfumes having substantially no trail (i.e. an average intensity lower than 1) were given a score "−".

Perfumes C, D, E, F, G and H were detected within 60 seconds in average and found to produce a coherent, fast developing and prolonged olfactory impact at a distance of 2 m, whereas the coherence and development speed were found to increase with increasing intensity. On the contrary, perfumes A and B, which were not obeying the composition rules according to the present invention were found to produce an incoherent olfactory impact at a distance of 2 m, i.e. the perfume did not reach a maximum odour intensity could not be recognized by the skilled panelists within the time frame of the measurement. Only perfumes C, D, E, F, G and H can be considered as having coherent, fast developing and prolonged olfactory impact at a distance from the compositions' source, when submitted to convection flows

TABLE 2

Perfume compositions and trail scores

| Perfumes | A | B | C | D | E | F | G | H |
|---|---|---|---|---|---|---|---|---|
| (E)-9-hydroxy-5,9-dimethyldec-4-enal | | | | 8.3 | | | 3.9 | |
| N-ethyl-N-(m-tolyl)-propionamide | | 5 | | | | | | |
| 3,8,8,11a-tetramethyldodecahydro-1H-3,5a-epoxynaphtho[2,1-c]oxepine | | | | | | 0.3 | 0.3 | |

TABLE 2-continued

Perfume compositions and trail scores

| Perfumes | A | B | C | D | E | F | G | H |
|---|---|---|---|---|---|---|---|---|
| 1,3,4,5,6,7-hexahydro-beta.,1,1,5,5-pentamethyl-2H-2,4a-methanonaphtalene-8-ethanol | | | 0.2 | 0.5 | | | | 1.5 |
| (Z)-oxacycloheptadec-10-en-2-one | 0.5 | | | | | | | |
| 2,5,5-trimethyl-1,2,3,4,4a,5,6,7-octahydronaphthalen-2-ol | | | | 0.1 | | | | |
| 3a,6,6,9a-tetramethyldodecahydronaphtho[2,1-b]furan | 0.1 | | | | 1.1 | 0.2 | 0.2 | |
| (E)-1-methoxy-4-(prop-1-en-1-yl)benzene | | | | | 1 | | | |
| (1R,2S,4R)-2'-isopropyl-1,7,7-trimethylspiro[bicyclo[2.2.1]heptane-2,4'-[1,3]dioxane] | | | | | 0.9 | | | |
| benzyl benzoate | | | | | 5.6 | | | 20 |
| benzyl 2-hydroxybenzoate | 4 | | | | | | | |
| octahydro-2H-chromen-2-one | | | 1.7 | | | | | |
| ((1S,8aR)-1,4,4-trimethyl-2,3,3a,4,5,8-hexahydro-1H-5,8a-methanoazulen-6-yl)methanol | | 4 | | | | | | |
| 3,7-dimethyloct-6-en-1-ol | | | 1 | | | 2.8 | 2.8 | |
| (Z)-3-methylcyclotetradec-5-enone | | | | 6.1 | 1.1 | 1.1 | 1.1 | |
| 2H-chromen-2-one | | | | 2.2 | 2.2 | | | 5.5 |
| dimethyl benzene-1,2-dicarboxylate | | | | 10.3 | | | | |
| 2-(sec-butyl)-1-vinylcyclohexyl acetate | | 8 | | | | | | |
| 2,6-dimethyloct-7-en-2-ol | | | 10 | 3 | 8.9 | 2.8 | 2.8 | |
| dipropylene glycol | | | | 5.3 | 9.6 | | | |
| (E)-3-methyl-5-(2,2,3-trimethylcyclopent-3-en-1-yl)pent-4-en-2-ol | | | | | | | | 2.5 |
| 3-ethoxy-4-hydroxybenzaldehyde | | | | 1.7 | | | | 1.5 |
| 1,4-dioxacycloheptadecane-5,17-dione | 5 | | | | | | | 8 |
| 4-allyl-2-methoxyphenol | | | | | 2.5 | | | |
| (E)-7,11-dimethyl-3-methylenedodeca-1,6,10-triene | | 8 | | | | | | |
| 4,6,6,7,8,8-hexamethyl-1,3,4,6,7,8-hexahydrocyclopenta[g]isochromene | | 6 | | | | | | |
| 1-(1,2,8,8-tetramethyl-1,2,3,4,5,6,7,8-octahydronaphthalen-2-yl)ethanone | | | | | 22.2 | | | |
| (E)-3,7-dimethylocta-2,6-dien-1-ol | | | | 0.5 | | | | |
| methyl 2-(3-oxo-2-pentylcyclopentyl)acetate | 35 | | 28 | 50 | | 16.7 | 16.7 | |
| benzo[d][1,3]dioxole-5-carbaldehyde | 0.1 | | | | | | | |
| 2-butyl-4,4,6-trimethyl-1,3-dioxane | | 5 | | | | | | |
| methyl 7-isopropyl-1,4a-dimethyl-1,2,3,4,4a,4b,5,6,7,8,10,10a-dodecahydrophenanthrene-1-carboxylate | | 5 | | | | | | |
| methyl 2,4-dihydroxy-3,6-dimethylbenzoate | | | | 1.1 | | | | |
| 1H-indole | 0.1 | | | | | | | |
| 1-(2,3,8,8-tetramethyl-1,2,3,4,5,6,7,8-octahydronaphthalen-2-yl)ethanone | 16 | | | | | | | |

TABLE 2-continued

Perfume compositions and trail scores

| Perfumes | A | B | C | D | E | F | G | H |
|---|---|---|---|---|---|---|---|---|
| (1-methyl-2-((1,2,2-trimethylbicyclo[3.1.0]hexan-3-yl)methyl)cyclopropyl)methanol | | | | | 0.2 | | | 0.2 |
| 3-(4-(tert-butyl)phenyl)-2-methylpropanal | | | | | | 2.8 | 2.8 | |
| 1-methyl-4-(prop-1-en-2-yl)cyclohex-1-ene | | | 3.9 | | 10 | | | |
| 3,7-dimethylocta-1,6-dien-3-ol | | | 1.5 | | | 1.1 | 1.1 | |
| 3,7-dimethylocta-1,6-dien-3-yl acetate | | 10 | 2 | | | | | |
| 3-methyl-5-phenylpentan-1-ol | | | | | 2.8 | | | |
| methyl 2-aminobenzoate | | | | | | 0.1 | 0.1 | |
| cyclopentadecanone | 1.5 | | | | | | | |
| 1-(4-(tert-butyl)-2,6-dimethyl-3,5-dinitrophenyl)ethanone | | | | | | 0.4 | 0.4 | |
| (Z)-3,7,11-trimethyldodeca-1,6,10-trien-3-ol | | 10 | | | | | | |
| (E)-13-methyloxacyclopentadec-10-en-2-one | | | 17 | | | | | |
| 7-methoxy-3,7-dimethyloctan-2-ol | | | 6 | | | | | |
| 4-(tert-butyl)cyclohexanol | | | 5 | | | | | |
| (1-methyl-2-(((1R,3R)-2,2,3-trimethylcyclopentyl)methyl)cyclopropyl)methanol | | | | | 8.3 | 6.1 | | |
| Patchouli oil | 0.2 | | 0.2 | | | | | |
| 3,7-dimethylocta-1,6-dien-3-yl dimethylcarbamate | | | | | 6.1 | 6.1 | 6.1 | |
| 2-cyclohexylidene-2-(o-tolyl)acetonitrile | | | 8 | | 8 | | | |
| 2-phenoxyethanol | | 8 | | | | | | |
| 6,6-dimethyl-2-methylenebicyclo[3.1.1]heptane | | | 0.5 | | | | | |
| (2E,5E)-5,6,7-trimethylocta-2,5-dien-4-one | | | 2 | | | | | |
| (E)-2-ethyl-4-(2,2,3-trimethylcyclopent-3-en-1-yl)but-2-en-1-ol | | | 2 | | | | | |
| 2-(cyclohexylmethyl)-4,4,6-trimethyl-1,3-dioxane | | 10 | | | | | | |
| (E)-2-methyl-4-(2,2,3-trimethyl-1-cyclopent-3-enyl)but-2-en-1-ol | | | 5 | | | | | |
| 2-(1-(3,3-dimethylcyclohexyl)ethoxy)-2-methylpropyl cyclopropanecarboxylate | | | | | 10 | | | |
| oxacyclohexadecan-2-one | 4 | | | | | | | |
| 1-(cyclopropylmethyl)-4-methoxybenzene | | | 0.4 | | | | | |
| triethyl 2-hydroxypropane-1,2,3-tricarboxylate | | | | 4.6 | | | | |
| 3-(benzo[d][1,3]dioxol-5-yl)-2-methylpropanal | 1 | | 3 | 3.9 | | 2.8 | 2.8 | |
| 4-hydroxy-3-methoxybenzaldehyde | 0.02 | | | 1.7 | 1.7 | | | |
| 1-((1S,8aS)-1,4,4,6-tetramethyl-2,3,3a,4,5,8-hexahydro-1H-5,8a-methanoazulen-7-yl)ethanone | | | | | | | | 20 |
| INGREDIENTS NOT INCLUDED IN ANY OF GROUP 2, 3, 4 and 5 | 26.48 | 22 | | | | 62.8 | 58.9 | 40.8 |
| SUM PERCENTAGE | 100 | 100 | 100 | 100 | 100 | 100 | 100 | 100 |
| SUM GROUP 2 | 73.52 | 8 | 66.8 | 73.8 | 49.1 | 24.4 | 28.4 | 39.2 |
| SUM GROUP 3, 4, 5 | 1.8 | 0 | 11.8 | 13.8 | 17.1 | 2.1 | 6 | 8.7 |
| SUM GROUP 5 | 0.02 | 0 | 1.9 | 5.5 | 3.9 | 0.7 | 0.7 | 8.5 |
| AVERAGE INTENSITY SCORE CLASS | − | − | + | +++ | ++ | + | ++ | +++ |

The invention claimed is:

1. A method of evaluating the spatio-temporal attributes of a perfume composition, said method comprising the steps of:
   generating a directional air flow in which a perfume composition source is placed;
   entraining the perfume composition in said air flow to provide a scented plume in which the composition is substantially confined; and
   directing the scented plume along a channel towards an aperture in said channel at a defined distance from the source, at which aperture said scented plume can be smelled and evaluated,
   wherein the top of the channel is open to enable an evaluator to evaluate the scented plume at different distances along the channel, and wherein the evaluation is performed at a distance greater than 0.5 meters.

2. The method according to claim 1, wherein the evaluation is performed after the perfume composition has been allowed to evaporate for a certain period of time at a temperature of 32±2° C.

3. The method of claim 2, wherein the period of time is at least 30 minutes.

4. The method of claim 3, wherein the period of time is at least 1 hour.

5. The method of claim 4, wherein the period of time is at least 2 hours.

6. The method of claim 5, wherein the period of time is at least 4 hours.

7. The method according to claim 1, wherein the evaluation is performed at a distance greater than 1 meter.

8. The method according to claim 7, wherein the evaluation is performed at a distance greater than 1.5 meters.

9. The method according to claim 8, wherein the evaluation is performed at a distance greater than 2 meters.

10. The method according to claim 1, wherein the evaluation procedure involves the steps of:
    allowing a perfume sample evaporating for a time interval T1 in an open environment, at a temperature of from 20 to 35° C., T1 being longer than 30 minutes,
    inserting said sample into a device, which has been maintained at a temperature of 32±2° C.,
    evaluating the olfactory characteristics and intensity of the smell at the output of the channel as a function of time, and,
    after a time interval T2, optionally evaluating the olfactory characteristics and intensity of the smell at different locations on top of the channel, starting from the output and moving downstream, within a time interval T3.

11. The method according to claim 1, wherein the evaluation of the olfactory attributes comprises olfactory intensity, olfactory impact, odour description, sharpness, transparency, presence, and/or volume.

12. The method according to claim 1, wherein the perfume composition is applied onto a substrate at a concentration of 10% by weight in a solvent.

* * * * *